United States Patent
Manion et al.

(10) Patent No.: US 10,881,622 B2
(45) Date of Patent: Jan. 5, 2021

(54) SMART TRANSDERMAL MICRODISPENSING SYSTEM FOR INTEGRATED WEIGHT MANAGEMENT

(71) Applicant: Xinova, LLC, Seattle, WA (US)

(72) Inventors: Michael Keoni Manion, Seattle, WA (US); Stephanie Brunelle, Seattle, WA (US)

(73) Assignee: Xinova, LLC, Seattle, WA (US)

( * ) Notice: Subject to any disclaimer, the term of this patent is extended or adjusted under 35 U.S.C. 154(b) by 253 days.

(21) Appl. No.: 16/132,492

(22) Filed: Sep. 17, 2018

(65) Prior Publication Data

US 2020/0085761 A1    Mar. 19, 2020

(51) Int. Cl.
*A61K 9/70* (2006.01)
*A61M 31/00* (2006.01)
*G16H 20/10* (2018.01)

(52) U.S. Cl.
CPC ......... *A61K 9/7092* (2013.01); *A61M 31/002* (2013.01); *A61M 2205/35* (2013.01); *G16H 20/10* (2018.01)

(58) Field of Classification Search
CPC .... A61K 45/06; A61K 31/198; A61K 31/485; A61K 36/185; A61K 36/48;
(Continued)

(56) References Cited

U.S. PATENT DOCUMENTS 6,689,380 B1 * 2/2004 Marchitto ............. A61M 37/00 424/422
6,723,086 B2    4/2004 Bassuk et al.
(Continued)

FOREIGN PATENT DOCUMENTS

CA         2668184 A1     5/2008
WO    2008054788 A2     5/2008

OTHER PUBLICATIONS

"Global Fitness App Market Growth of 31.35% CAGR by 2020—Analysis, Technologies & Forecast Report 2016-2020—Key Vendors: Adisas, Nike, Under Armour—Research and Markets," Business Wire, accessed at https://web.arhive.org/web/20170521030206/http://www.businesswire.com/news/home/20160229006652/en/Global-Fitness-App-Market-Growth-31.35-CAGR. pp. 03 (Feb. 29, 2016).

(Continued)

*Primary Examiner* — Manuel A Mendez
(74) *Attorney, Agent, or Firm* — Hertzberg, Turk & Associates, LLC

(57) ABSTRACT

Technologies are described for delivery of compounds to aid in weight management. A transdermal microdispenser based system may deliver weight management compounds through the time and dose specific administration of appetite suppression, metabolic enhancers, and satiation compounds. The transdermal delivery system may be controlled based on data associated with subject such as calorie intake, physical activity, satiation, and hunger. The system may be integrated with medical monitoring or fitness tracking systems. Delivery of the compounds may be distributed over the course of a day at selected or adjusted doses to be safe and effective for their specific modality. For example, appetite suppressants may be delivered during periods of the day when cravings occur, satiation compounds may be delivered to coincide with meals, and metabolic stimulators may be delivered at times to optimally increase metabolism based on caloric balance. Control factors may also be predictive to prevent the onset of hunger.

27 Claims, 10 Drawing Sheets

(58) Field of Classification Search
CPC ............... A61K 31/522; A61M 5/1723; G06F 19/3456; G06F 19/3475; G09B 19/0092; A61B 5/4839
See application file for complete search history.

(56) References Cited

U.S. PATENT DOCUMENTS

| | | |
|---|---|---|
| 8,372,040 B2 | 2/2013 | Huang et al. |
| 2003/0208113 A1 | 11/2003 | Mault et al. |
| 2008/0220092 A1 | 9/2008 | DiPierro et al. |
| 2009/0259176 A1 | 10/2009 | Yairi |
| 2012/0302942 A1 | 11/2012 | DiPierro et al. |
| 2014/0323423 A1 | 10/2014 | DiPierro et al. |
| 2015/0144653 A1* | 5/2015 | Kline .................. B67D 1/0888 222/1 |
| 2017/0224911 A1* | 8/2017 | DiPierro .............. A61K 31/485 |

OTHER PUBLICATIONS

Smith, C., "Global Weight Management Market Is Expected to Reach USD 314.7 Bn by 2024—Credence Research," PDF Devices, accessed at https://web.archive.org/web/20170217213253/https://www.pdfdevices.com/global-weight-management-market-is-expected-to-reach-usd-314-7-bn-by-2024-credence-research/, accessed on Feb. 17, 2017, accessed on Jul. 19, 2018, pp. 4.

Woos, S.C., and D'Alessio, D.A., "Central control of body weight and appetite," The Journal of Clinical Endocrinology and Metabolism, vol. 93, No. 11, pp. s37-s50 (Nov. 1, 2008).

\* cited by examiner

COMPUTER PROGRAM PRODUCT 1000

SIGNAL BEARING MEDIUM 1002

1004 ONE OR MORE INSTRUCTIONS TO:

DETERMINE A DOSAGE FOR THE DELIVERY OF THE PLURALITY OF COMPOUNDS; DETERMINE A TIMING FOR THE DELIVERY OF THE PLURALITY OF COMPOUNDS; AND DELIVER THE PLURALITY OF COMPOUNDS BASED ON THE DETERMINED DOSAGE AND THE DETERMINED TIMING

| COMPUTER-READABLE MEDIUM 1006 | RECORDABLE MEDIUM 1008 | COMMUNICATIONS MEDIUM 1010 |
|---|---|---|

SMART TRANSDERMAL MICRODISPENSING SYSTEM FOR INTEGRATED WEIGHT MANAGEMENT

BACKGROUND

Unless otherwise indicated herein, the materials described in this section are not prior art to the claims in this application and are not admitted to be prior art by inclusion in this section.

Increase of obesity and consequently associated diseases has reached epidemic proportions in many countries around the world, but more critically in the United States, where obesity rates have increased from 23% of adults in 1962 to almost 40% of adults in 2016. Obese and overweight individuals are often associated with a higher risk of coronary heart disease, diabetes, and other chronic conditions creating a substantial burden on national health systems and economies.

Weight management compounds may be delivered in some cases transdermally. For example, delivery through a dermal patch is commonly implemented. One may place a patch containing a weight management compound on the skin, which may deliver the compound over a predefined (e.g., 24-hour) period. However, the delivered dose may typically decrease toward the end of the application period. Such as release profile may not match the metabolic and/or appetite control needs of the person throughout the day. Metabolism and satiation/hunger involve complex physiological and psychological responses, and weight management efficacy may be reduced if combination, timing, and dosage of weight management compounds are not selected and controlled carefully. Furthermore, the dermal patches deliver a set dose of the weight management compounds, which may not be the right concentration for a given individual, and the dosage requirements may change over the course of a weight management program.

SUMMARY

The present disclosure generally describes techniques for a delivery of compounds to aid in weight management.

According to some examples, a transdermal dispensing apparatus for a delivery of compounds to aid in weight management may include a processor configured to determine a dosage for individual delivery of the compounds, and determine a timing for the individual delivery of the compounds. The apparatus may also include a dispensing unit communicatively coupled to the processor configured to deliver the compounds transdermally based on the determined dosage and the determined timing.

According to other examples, a system for a delivery of compounds to aid in weight management may include a controller configured to analyze information associated with a subject, determine a dosage for individual delivery of the compounds based on the analysis, and determine a timing for the individual delivery of the compounds based on the analysis. The system may also include a delivery apparatus that includes a storage unit, a processor configured to receive the determined dosage and the determined timing from the controller, and a dispensing unit configured to deliver the compounds transdermally based on the determined dosage and the determined timing.

According to further examples, a method for a delivery of compounds to aid in weight management may include receiving the compounds, determining a dosage for individual delivery of the compounds, determining a timing for the individual delivery of the compounds, and delivering the compounds transdermally based on the determined dosage and the determined timing.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 10 illustrates a block diagram of an example computer program product, all arranged in accordance with at least some embodiments described herein.

DETAILED DESCRIPTION

Figure 1:
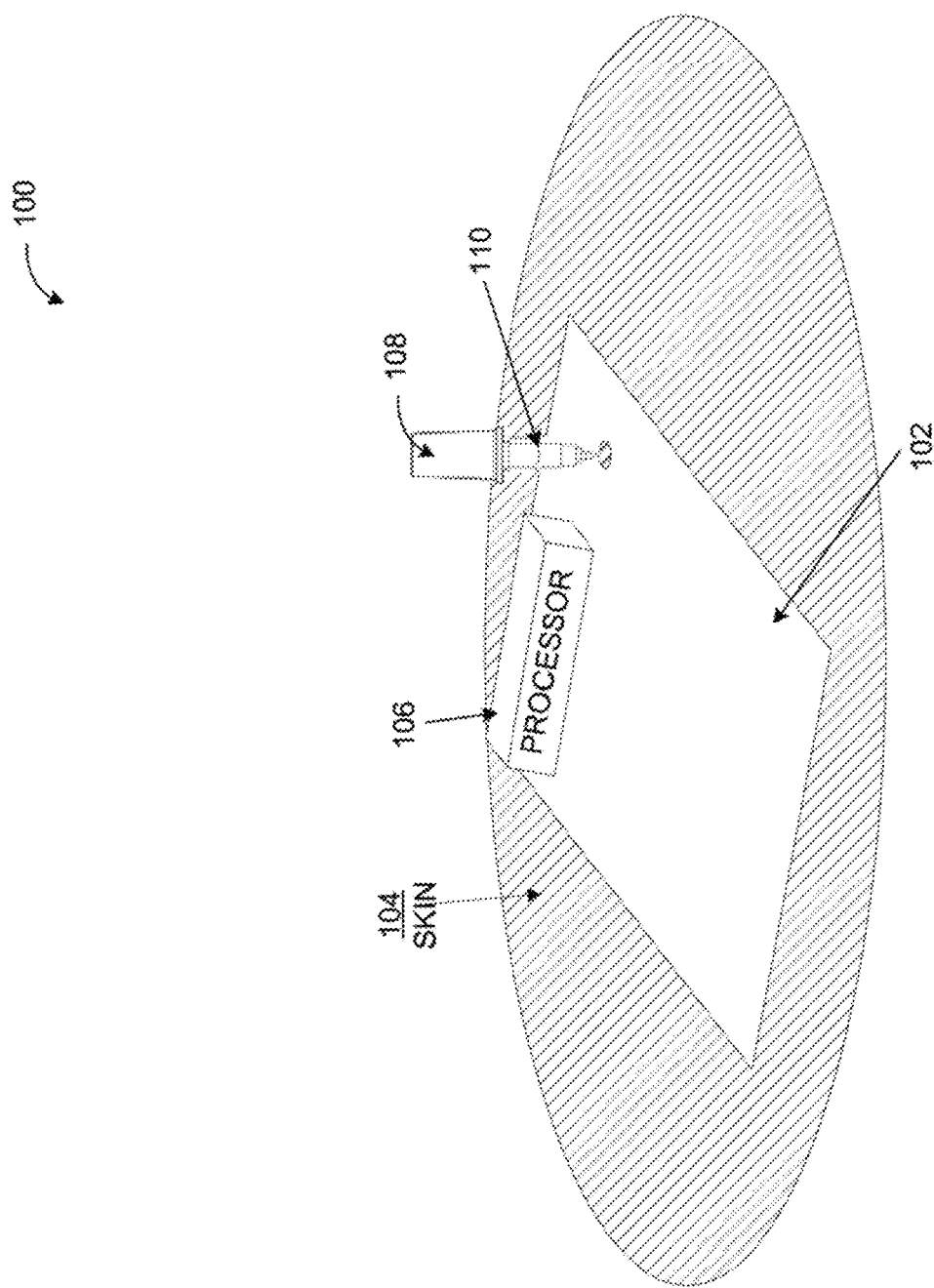
FIG. 1 includes an example dispensing apparatus for a delivery of compounds to aid in weight management.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and/or computer program products related to the delivery of compounds to aid in weight management.

Briefly stated, technologies are generally described for delivery of compounds to aid in weight management. A transdermal microdispenser based system may deliver weight management compounds through the time and dose specific administration of appetite suppression, metabolic enhancers, and satiation compounds. The transdermal delivery system may be controlled based on data associated with subject such as calorie intake, physical activity, satiation, and hunger. The system may be integrated with medical monitoring or fitness tracking systems. Delivery of the compounds may be distributed over the course of a day at selected or adjusted doses to be safe and effective for their specific modality. For example, appetite suppressants may be delivered during periods of the day when cravings occur, satiation compounds may be delivered to coincide with meals, and metabolic stimulators may be delivered at times to optimally increase metabolism based on caloric balance. Control factors may also be predictive to prevent the onset of hunger.

FIG. 1 includes an example dispensing apparatus for a delivery of compounds to aid in weight management, arranged in accordance with at least some embodiments described herein.

As discussed above, fixed dosage and timing patch or oral delivery mechanisms may not match metabolic or appetite control needs of a person throughout the day. Metabolism as well as satiation include complex physiological and psychological responses that may vary widely between individuals. In other words, a delivery mechanism may be very effective for a first person, and a second person may experience no effect. The embodiments detailed below describe a dynamic system for the delivery of compounds to aid in weight management that may be tailored to the needs of the person. Data and information associated with the person may be collected and used to optimize the efficacy of the plurality of weight management compounds by determining optimal dosages and timings. In turn, more effective therapies may be produced, and patient outcomes may be improved through the implementation of the embodiments described below. Delivery devices may be wearable or usable at the point of care clinic depending on the types of compounds.

Figure 3:
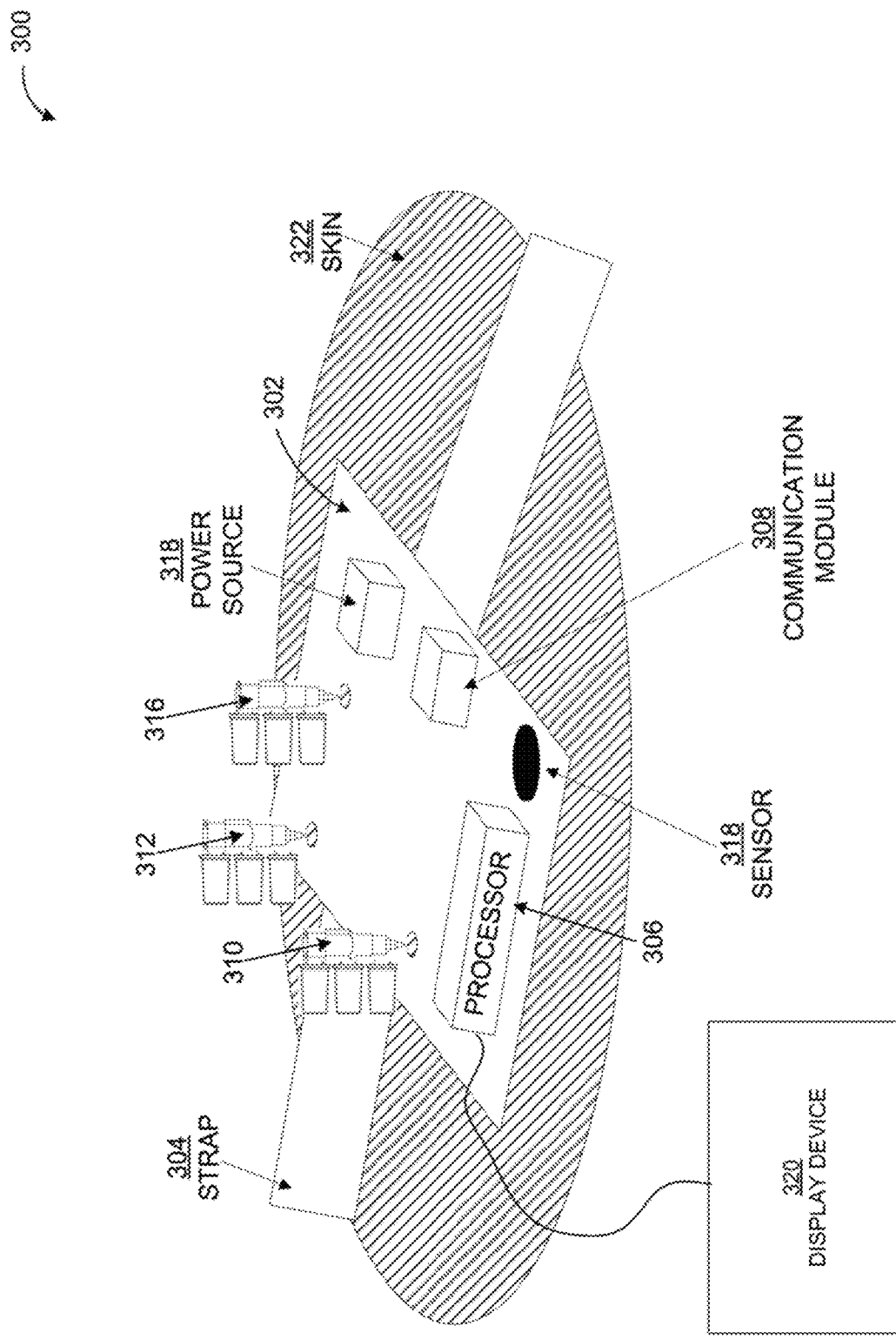
FIG. 3 includes an example dispensing apparatus that may be worn by a subject.

In an example scenario, a person may be overweight or obese, and a physician or registered dietician may recommend the person begin a weight management regimen that includes receiving compounds to aid in weight management. For example, the physician or registered dietician may recommend that the person receive an appetite suppressant, a metabolic stimulant, and a satiating compound in order to complement other weight management strategies and assist the person in reaching a weight management goal. As shown in diagram 100, the physician may attach an apparatus 102 to the skin 104 of the person to deliver the compounds to the person. For example, in diagram 100 the apparatus 102 may be attached to the skin 104 by an adhesive layer. The adhesive layer may be designed or intended for a single use or may be reusable. In some embodiments, the apparatus 102 may be attached to the skin 104 using a separate adhesive, such as surgical tape or a specialty glue, worn as shown in FIG. 3, or attached to the person by stitching or staples. According to other examples, the apparatus 102 may be an oral delivery device, a nasal delivery device, a sublingual delivery device, a buccal delivery device, an ocular delivery device, an otic delivery device, a rectal delivery device, a vaginal delivery device, an intravenous delivery device, an intramuscular delivery device, a subcutaneous delivery device, an intradermal delivery device, an intrathecal delivery device, a cutaneous delivery device, a nebulizer, or an inhaler. Apparatus 102 may also be in a surgical setting, where a therapeutic may be to be delivered in-vivo for an immediate intervention with a tightly controlled dosage.

The apparatus 102 may include a processor 106, a cartridge 108, and a dispensing unit 110. The processor 106 may be a controller that is configured to determine a dosage for the delivery of each of the compounds and determine a timing for the delivery of each of the compounds. Returning to the example discussed above, a physician may recommend that the person receive an appetite suppressant, such as diethylpropion, oxymetazoline, phentermine, rimonabant, sibutramine, bitter orange, chromium, forskolin, hydroxycitric acid, glucomannan, guar gum, or hoodia, between mealtimes. The physician may also recommend the person receive a metabolic stimulator such as caffeine, bitter orange, calcium, chromium, conjugated linoleic acid, fucoxanthin, green coffee bean extract, pyruvate, raspberry ketone, white kidney bean, yohimbe, L-Tyrosine, L-Carnitine, green tea, resveratrol, nootkatone, or capsaicin, based on a comparison of an actual calorie intake and a recommended calorie intake. Furthermore, the physician may recommend the person receive a satiating compound such as cholecystokinin, glucagon-like peptide 1, peptide YY, oxyntomodulin, apolipoprotein A-IV, enterostatin, bombesin-family peptides such as gastrin-releasing peptide and neuromedin B, amylin, leptin, glucomannan, guar gum, or chitosan, during a mealtime. In some examples, the compounds may include more than one appetite suppressant, more than one metabolic stimulator, or more than one satiation compound. In other examples, excipients may be included in delivery to enhance the penetration and absorption efficiency.

In order to determine the timing and dosage for the delivery of each of the compounds, the processor 106 may receive information about the person. The information associated with the person may include a current weight, a goal weight, a recommended calorie intake, an actual calorie intake, a recommended calorie expenditure, an actual calorie expenditure, a sleep schedule, a circadian rhythm of the subject, one or more average mealtimes for the subject, an average temperature based on the circadian rhythm, a basal metabolic rate (BMR) of the subject, or a metabolic rate based on the circadian rhythm. In the example scenario, the physician may ask the person about their daily routine and determine average mealtimes based on the person's response, such as 8:30 AM, 1:00 PM, and 7:00 PM. The physician may weigh the person to determine an initial or current body weight for the person. For example, the person's initial weight may be 160 kg. The person and physician may determine a goal weight for the person based on the person's needs or other health factors. In some embodiments, the processor 106 may determine the goal weight.

The physician may also recommend a diet to the person that includes a recommended calorie intake. The recommended calorie intake may be based on a period of time such as an hourly, daily, or weekly calorie intake. The recommended calorie intake may be based on a daily caloric need of the person. For example, the physician may calculate a calorie need for the person, such as 2,000 calories per day, that describes a neutral caloric intake meaning no weight is gained or lost. Based on the neutral caloric intake, the physician may recommend a calorie intake of 1,800 calories per day, which may cause the person to lose weight. In other situations, the person may need to gain weight and the recommended calorie intake may be higher than the calorie need for the person. The recommended diet may also include recommended percentages of calories from macronutrients or recommended quantities of each macronutrient. For example, the physician may recommend that 35% of the recommended calorie intake should come from carbohydrates, 20% of the recommended calorie intake should come from fats, and the remaining 45% should come from proteins. The physician may provide further recommendations for particular types of carbohydrates, fats, and proteins. For example, the physician may recommend the person consume only 50 grams (g) of added sugar per day or 25 g of saturated fat per day. In other embodiments, the physician may recommend consumption targets for micronutrients, such as vitamins and minerals. The recommended calorie intake may be adjusted throughout the weight management regimen based on the weight management goals of an individual or other collected information associated with the subject.

In some examples, the physician may include a recommended calorie expenditure to the person. The recommended calorie expenditure may be based on the BMR of the person and the recommended calorie intake for the person. The recommended calorie expenditure may include a recommended exercise regimen in order to burn a specific number of calories per day. For example, the physician may recommend that the person expend at least 500 calories per day. The person may expend the calories by walking at least 10,000 steps per day and may track their steps using a pedometer or another device, such as a fitness watch. In some examples, the apparatus 102 may include components to collect information about the person. The recommended calorie expenditure may be adjusted throughout the weight management regimen based on the weight management goals of the individual or other collected information associated with the subject.

In some embodiments, the physician may recommend a sleep schedule to the person. The sleep schedule may be intended to maintain a regular circadian rhythm for the person in order to maximize the efficacy of the compounds. For example, the prescribed metabolic stimulator may be delivered to the person during a known period of sleep in order to encourage the person's body to burn more calories. In turn, the person's BMR may increase, thus creating a larger calorie deficit and leading to weight management. In other examples, a sleep model may be used to determine timing and dosage of delivered compounds. For example, a basic sleep model may include a time range when the person is asleep. The sleep model may be estimated or determined by the device. Weight management compounds may not be needed during a sleep period, they may be delivered at or slightly before the person wakes up. The weight management compounds may also be delivered prior to sleep period.

The physician may transmit the determined mealtimes, dosages per kg of body weight of each of the compounds, the person's initial weight, and the recommended daily calorie intake to the processor 106. In order to transmit the information about the person, the physician may enter the values for the determined mealtimes, dosages per kg of body weight of each of the compounds, the person's initial weight, and the recommended daily calorie intake using a computing device (e.g., a server, a desktop computer, a mobile computer, a special purpose computing device, a laptop, a smart phone, or even a component level processor).

In some embodiments, the processor 106 may be communicatively coupled to the computing device, and the computing device may transmit the information to the processor after the information has been entered. In other examples, the processor 106 or the apparatus 102 may be configured to receive the values directly through an input. According to other embodiments, a protocol for the delivery of the compounds may be transmitted to the processor 106. The protocol may include pre-determined dosages and timings for individual delivery of the compounds and may be updated as needed. For example, the processor 106 may update the protocol or an updated protocol may be provided to the processor 106. Control or adjustment factors may also be predictive to prevent the onset, for example, before a big meal the metabolism may be enhanced and similarly for other circumstances which may require intervention ahead of the event. Additionally, safety measures may be incorporated into the delivery mechanism. For example, blood sugar level may be monitored in conjunction with other monitored aspects of delivery timing/dosage to prevent the levels from dropping to dangerously low levels. Other health aspects may be similarly monitored and incorporated into the delivery timing/dosage determination.

The processor 106 may receive the information associated with the person, such as the determined mealtimes, dosages per kg of body weight of each of the compounds, the person's initial weight, and the recommended daily calorie intake. The processor may analyze the received information and determine a dosage and a timing for each of the compounds based on the analysis. For example, the processor 106 may determine that the appetite suppressant, which is to be delivered between mealtimes, may be delivered at 10:00 AM, 2:30 PM, and 8:30 PM. The processor 106 may also determine the dosage of the appetite suppressant based on the person's initial weight and the recommended dose per kg or body weight. For example, the person's initial weight may be 160 kg; the recommended dose of the appetite suppressant may be 1 milligram (mg) per kg of body weight; the recommended dose for the metabolic stimulator may be 0.5 mg per kg of body weight, and the recommended dose for the satiation compound may be 0.75 mg per kg of body weight. The processor 106 may receive those values and calculate the dosage of appetite suppressant to be 160 mg. Similarly, the processor 106 may determine the dosage for the metabolic stimulator to be 80 mg (0.5 mg/kg*160 kg) and may determine that the metabolic stimulator may be delivered at 12:00 AM if an actual calorie intake is higher than the recommended calorie intake. The processor 106 may determine the dosage of the satiation compound to be 120 mg (0.75 mg/kg*160 kg) and may determine that it may be delivered during each meal at 8:30 AM, 1:00 PM, and 7:00 PM.

Hunger may be predicted of several ways. One approach may include long-term averaging of caloric intake and timing to determine if patterns exist that may be preempted with an appetite suppressant. Another approach may include real-time or quasi-real-time monitoring, to predict when a caloric depression may result due to the person having burnt sufficient calories from a previous meal. The person's general activity level or changes in the level of attention/distraction may be monitored and/or bodily reactions such as stomach growling (hunger pangs) may be listened for. The monitoring may be performed in real-time or over longer time periods to inform the system of situations whether hunger may occur. There may be fluctuations throughout the day, differences with the day of the week or month, or even seasonal variations.

Figure 2:
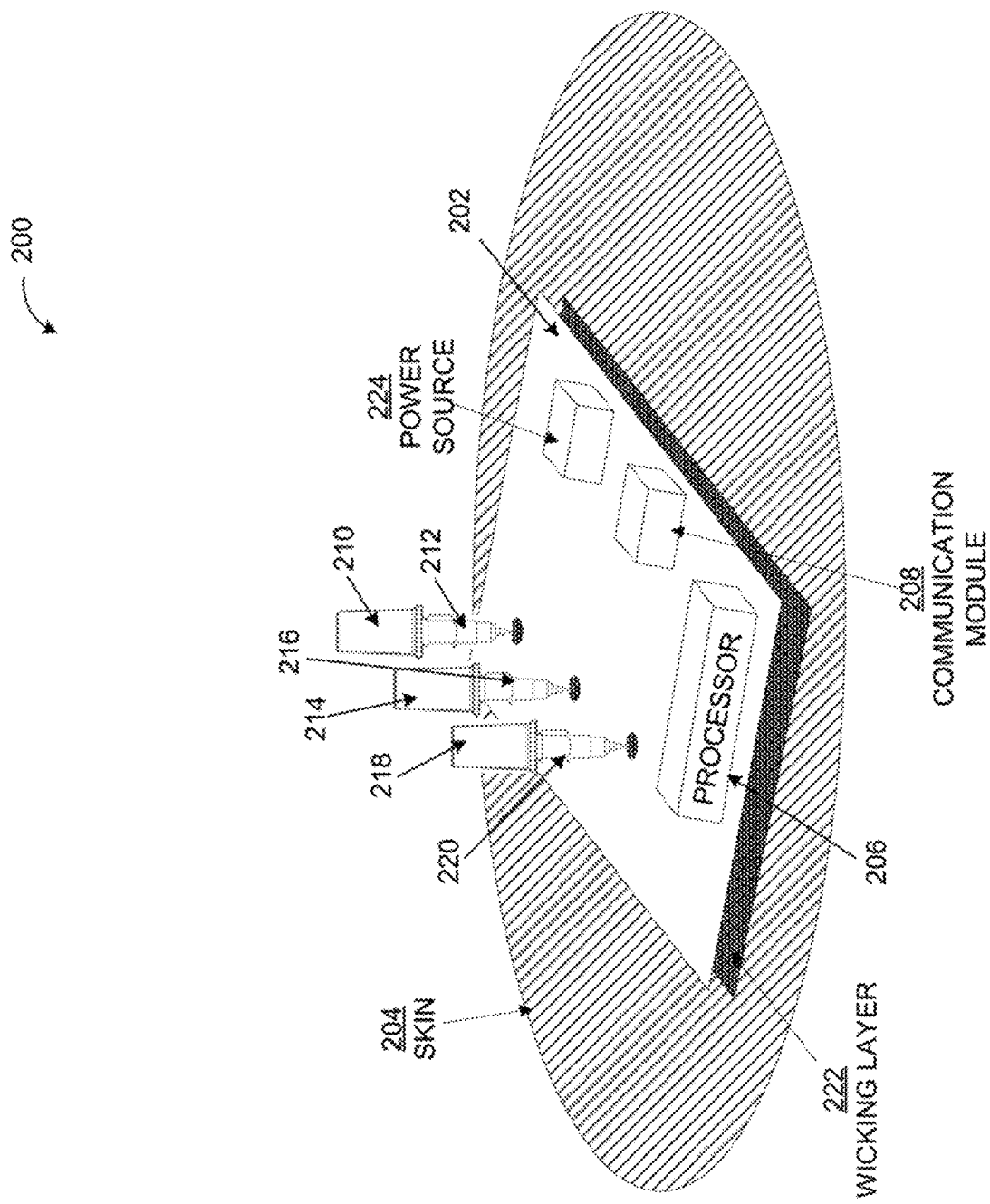
FIG. 2 includes an example dispensing apparatus with multiple dispensing units, a power source, a communication module, and a wicking layer.

As discussed above, the apparatus 102 may also include a cartridge 108. The cartridge 108 may store the compounds to be delivered to the person. According to some embodiments, the cartridge 108 may store all of the prescribed compounds as shown in diagram 100, and in other embodiments, the apparatus may include two or more cartridges to store the compounds, as shown in FIGS. 2 and 3. In some examples, the cartridge 108 may receive the compounds to be stored and may be refilled as needed. According to other examples, the cartridge 108 may be a single use cartridge and may be replaced as needed. As shown in diagram 100, the cartridge 108 may be coupled to the dispensing unit 110. In other embodiments, the cartridge 108 and the dispensing unit 110 may be separate components. For example, the cartridge 108 may be a separate wearable device that is connected to the apparatus 102 and the dispensing unit 110. The dispensing unit 110 may receive the compounds from the cartridge 108 individually, in sequence, or together. The dispensing unit 110 may temporarily store a fraction of each of the compounds. For example, the dispensing unit 110 may store a fraction of the appetite suppressant for an upcoming delivery.

The dispensing unit 110 may deliver the compounds based on the determined dosage and the determined timing, which may be received from the processor 106. The dispensing unit 110 may be one of a Joule-heating dispenser or a piezoelectric dispenser. A Joule-heating dispenser may contain a fraction of a compound in a reservoir of the dispensing unit 110, according to at least some embodiments. For example, the Joule-heating dispenser may store a fraction of an appetite suppressant in the dispensing unit's reservoir. The Joule-heating dispenser may apply energy to the dispensing unit's reservoir in the form of heat, which may cause parts of the compound in contact with the reservoir to evaporate, forming one or more vapor bubbles. The formation and collapse of the vapor bubbles may create a unidirectional dispensing action. In such embodiments, the amount of the compound dispensed may be dictated by the amount of energy applied to the reservoir of the dispensing unit or by the amount of time the energy is applied to the reservoir. In other embodiments, the dispensing unit 110 may be a piezo-electric dispenser. A piezo-electric dispenser may contain a fraction of one compounds of the compounds in a reservoir of the dispensing unit 110. An electrical potential may be applied to the dispenser resulting in a mechanical force proportional to the electrical potential to be applied to the fraction of the compound in the dispensing unit's reservoir. As a result, the compound may be extruded or dispensed through an orifice in the dispensing unit's reservoir.

The dispensing unit 110 may be further configured to deliver a compound based on a detection of a trigger indication by the processor 106, such as detecting that the current time corresponds with a determined timing for delivery of one of the compounds. According to some embodiments, the dispensing unit 110 may be configured to detect the current time and deliver the compounds independently based on the determined timings and dosages. Returning to the example discussed above, the processor may detect that the current time is 10:00 AM, which corresponds with the first determined time that the appetite suppressant is to be delivered. The processor 106 may detect the trigger indication and transmit a signal to the dispensing unit 110 that the trigger event has occurred. The dispensing unit 110 may receive the signal and deliver 1 mg of the prescribed appetite suppressant directly onto the skin 104 such that the appetite suppressant is absorbed transdermally.

According to some embodiments, the dispensing unit 110 may deliver a compound onto a wicking layer, as shown in FIG. 2. The dispensing unit 110 may deliver the appetite suppressant, the satiation compound, and the metabolic stimulator based on the determined timings and dosages, based on the determined timing, determined dosage, and in response to the detection of the trigger event, or based on a determined dosage and a trigger event.

As described above, the trigger event may include a current time matching one of the determined timings for the delivery of the compounds. Additionally, the apparatus 102 may be configured to receive inputs and detect the inputs as trigger indications. For example, the apparatus 102 may further include a manual input such as a button, a switch, a touch screen, or the like. The apparatus 102 may also be configured to receive an input wirelessly from another device, such as another computing device (e.g., a server, a desktop computer, a mobile computer, a special purpose computing device, a laptop, a smart phone, or even a component level processor). Returning to the above example, the apparatus 102 may be connected to an application running on a mobile device that is owned by the person. Following the first dose of the appetite suppressant at 10:00 AM, the person may grow hungry at 10:45 AM. The person may open the application on their mobile device and enter an input indicating a time of craving. In response, the processor 106 may receive the input and detect a second trigger indication. In response, the dispensing unit 110 may deliver 1 mg of appetite suppressant to the skin 104 to be absorbed transdermally. In some embodiments, the processor 106 may receive a limit for each of the compounds and may prevent delivery of a compound if the limit for the compound has been reached. For example, the limit of the appetite suppressant in a 24-hour period may be 3 mg. The processor 106 may receive the aforementioned input from the application executed on the person's mobile device indicating hunger and may detect a trigger indication. The processor 106 may also detect the limit for the appetite suppressant has been reached and in response, may not transmit a signal to the dispensing unit 110 to deliver the appetite suppressant.

The received inputs may also include updated information or collected data associated with the person, such as a current weight, an updated goal weight, an actual calorie intake, an updated mealtime, an updated sleep schedule, an updated recommended calorie expenditure, or other health-related information. The processor 106 may be configured to extract data associated with the inputs and update the dosage or timing based on the extracted data. For example, the processor 106 may receive daily inputs that include a current weight of the person. The person may, on average, lose 1 kg each day the apparatus 102 is attached to the skin 104. Ten days after the apparatus 102 was attached to the skin 104, the processor 106 may receive data associated with the person that includes a current weight of 150 kg from a scale with wireless connectivity. The processor 106 may extract the value for the current weight and may update the dosages for the appetite suppressant, the satiation compound, and the metabolic stimulator based on the extracted data, which includes the current weight. In the example scenario described above, the dosages for the appetite suppressant, the satiation compound, and the metabolic stimulator may be updated to 150 mg, 75 mg, and 112.5 mg, respectively. In another example, the person may adopt a new daily routine that causes their average mealtimes to be changed to 6:30 AM, 12:00 PM, and 6:00 PM. As discussed above, the apparatus 102 may include a manual input, such as a touch screen, and the person may enter the new average mealtimes using the touch screen. The processor 106 may receive the updated mealtimes for the person and may update the timings for the appetite suppressant and the satiation compound to 8:00 AM, 1:30 PM, and 7:30 PM and 6:30 AM, 12:00 PM, and 6:00 PM, respectively. In a further example, the processor 106 may analyze the received data to determine an efficacy of the compounds and may update the dosages or timings based on the determined efficacy. The processor 106 may determine that one or more compounds may not be producing an intended effect and may determine one or more other compounds to be delivered to the person. The processor 106 may also provide information associated with the efficacy and the one or more other compounds to the person.

FIG. 2 includes an example dispensing apparatus with multiple dispensing units, a power source, a communication module, and a wicking layer, arranged in accordance with at least some embodiments described herein.

As shown in diagram 200, an apparatus 202 may be configured for the delivery of compounds to aid in weight management and may be attached to skin 204. The apparatus 202 may include a processor 206, a communication module 208, a first cartridge 210 coupled to a first dispensing unit 212, a second cartridge 214 coupled to a second dispensing unit 216, a third cartridge 218 coupled to a third dispensing unit 220, a wicking layer 222, and a power source 224. The apparatus 202 may be attached to the skin with an adhesive layer underneath the wicking layer 222. The adhesive layer may be intended for a single use or may be reusable.

In some examples, the processor 206 may be configured to receive information associated with a subject that the apparatus 202 is attached to via the communication module 208. For example, the processor 206 may receive information about the subject such as, a current weight, a goal weight, a recommended calorie intake, an actual calorie intake, a recommended calorie expenditure, an actual calorie expenditure, a sleep schedule, a circadian rhythm of the subject, one or more average mealtimes for the subject, an average temperature based on the circadian rhythm, a BMR of the subject, or a metabolic rate based on the circadian rhythm. The communication module 208 may receive the information associated with the subject from an input, such as a manual input. In some embodiments, the communication module 208 may be a network controller, which may be arranged to facilitate communications with one or more other computing devices over a network communication link via one or more communication ports. In an example scenario, the subject may make a new year's resolution to lose 25 pounds. The subject may weigh themselves, determine a recommended calorie intake in order to lose weight, and determine average mealtimes for breakfast, lunch, dinner. Moreover, the subject may take part in a study to determine a circadian rhythm, an average temperature based on the circadian rhythm, an average metabolic rate based on the circadian rhythm, a BMR, and a sleep schedule. The subject may enter the information into a web-based application, which may be uploaded to a server. The application may also be executed on a computing device, according to some examples.

The server may then transmit the information associated with the subject to the communication module 208, which may receive the information over a network. The communication module 208 may provide the received information to the processor 206. The processor 206 may receive the information associated with the person and recommend an appetite suppressant, such as diethylpropion, oxymetazoline, phentermine, rimonabant, sibutramine, bitter orange, chromium, forskolin, hydroxycitric acid, glucomannan, guar gum, or hoodia. The processor 206 may also recommend a metabolic stimulator, such as caffeine, bitter orange, calcium, chromium, conjugated linoleic acid, fucoxanthin, green coffee bean extract, pyruvate, raspberry ketone, white kidney bean, yohimbe, L-Tyrosine, L-Carnitine, green tea, resveratrol, nootkatone, or capsaicin. Furthermore, the processor 206 may recommend a satiating compound, such as cholecystokinin, glucagon-like peptide 1, peptide YY, oxyntomodulin, apolipoprotein A-IV, enterostatin, bombesin-family peptides such as gastrin-releasing peptide and neuromedin B, amylin, leptin, glucomannan, guar gum, or chitosan, during a mealtime. For example, the processor 206 may recommend the subject obtain forskolin (an appetite suppressant), pyruvate (a metabolic stimulator), and guar gum (a satiating compound).

The subject may obtain the recommended compounds or consult a doctor in order to be prescribed the compounds. The subject may obtain the compounds as solutions and may insert them into the first cartridge 210, the second cartridge 214, and the third cartridge 218. For example, the subject may load the forskolin solution into the first cartridge 210, the pyruvate solution into the second cartridge 214, and the guar gum solution into the third cartridge 218. The cartridges may be refillable and may be refilled periodically by the subject. In some examples, the subject may obtain cartridges that are pre-filled with the recommended or prescribed compounds and may be replaced as necessary.

In some examples, the processor 206 may be configured to detect a fill level of each cartridge. If the fill level for a cartridge falls below a certain threshold, such as 15%, or the processor 206 detects that a cartridge is empty, the processor 206 may signal the communication module 208 to notify the subject. In some examples, the processor 206 may be configured to directly notify the subject. The communication module 208 may transmit a signal to notify the subject to another computing device or to a display device. Returning to the example scenario described above, the communication module 208 may transmit a signal to the server, which may provide a notification to be presented to the user via the web-based application. The notification may be one of a textual or graphical notification. In other embodiments, the computing device that receives the signal from the communication module 208 may provide a notification directly to the subject. For example, the communication module 208 may transmit a signal to a mobile device of the subject, and the mobile device may present a notification to the user. In another example scenario, the communication module 208 may transmit the signal to a vendor or pharmacy to order a refill of a compound that corresponds to the almost empty or empty cartridge. In an example scenario, the processor 206 may detect that the first cartridge 210, which may have been pre-filled with forskolin, is below 15% full. The processor 206 may signal the communication module 208 that the first cartridge 210 is almost empty, and the communication module 208 may automatically place an order for a replacement cartridge. The subject may receive the replacement cartridge and replace the first cartridge 210.

The processor 206 may be further configured to determine a timing for the delivery of the compounds and determine a dosage for the delivery of the compounds based on the received information associated with the subject. In some examples, the processor 206 may additionally determine the dosage or timing based on information associated with the compounds to be delivered to the subject. For example, the processor 206 may determine a timing for the delivery of pyruvate (a metabolic stimulator) based on the received information associated with the subject, such as the subject's BMR, the circadian rhythm, or the average metabolic rate based on the circadian rhythm. The processor 206 may determine that the pyruvate is to be delivered at 3:00 AM based on a lower average metabolic rate at that time or based on the circadian rhythm of the subject. The processor 206 may determine a dosage for the delivery of the pyruvate. For example, the processor 206 may determine an initial dose based on the received information associated with the subject and based on information associated with pyruvate, such as a maximum dose or an optimal dose based on scientific literature. The processor 206 may receive the information associated with the compound, such as pyruvate, directly or via the communication module 208. The processor 206 may determine that 6 g of pyruvate is to be delivered to the subject. The processor 206 may determine a volume of solution to deliver based on the determined dosage and a concentration of a received solution. For example, the processor 206 may determine the 6 milliliters (mL) of pyruvate solution is to be delivered based on the determined dosage (6 g) and a concentration of the pyruvate solution stored in the second cartridge 214, which may be 1 g pyruvate per 1 mL of solvent. The processor 206 may transmit the determined dosages and timings to the first dispensing unit 212, the second dispensing unit 216, and the third dispensing unit 220 or may directly instruct the dispensing units (212, 216, and 220) to deliver the compounds based on the determined timings and dosages.

The first dispensing unit 212, the second dispensing unit 216, and the third dispensing unit 220 may be coupled to the first cartridge 210, the second cartridge 214, and the third cartridge 218, respectively. The first dispensing unit 212, the second dispensing unit 216, and the third dispensing unit 220 may receive the determined timings and determined dosages for the respective compounds stored in the first cartridge 210, the second cartridge 214, and the third cartridge 218. The dispensing units (212, 216, and 220) may deliver the compounds based on the determined timings and dosages. For example, the second dispensing unit 216 may receive the pyruvate from the second cartridge 214 and may dispense 6 mL of the pyruvate solution at 3:00 AM onto the wicking layer 222. The wicking layer 222 may be in contact with the skin 204 and may regulate the dosage of the compounds over time. For example, the wicking layer 222 may ensure the pyruvate dosage is delivered over the course of three hours from 3:00 AM to 6:00 AM rather than the entire dose being administered at 3:00 AM. The processor 206 may receive information associated with the properties of the wicking layer 222 and may determine dosages or timings for the delivery of the compounds based on the information associated with the wicking layer's 222 properties.

The communication module 208 may be further configured to receive updated information associated with the subject. The updated information may include an actual calorie intake, an updated mealtime, an indication of hunger, an updated sleep schedule, an updated circadian rhythm, or other relevant health information associated with the subject. For example, the subject may upload a value for their actual calorie intake each day. The communication module 208 may transmit the updated information to the processor 206. Based on the updated information, the processor 206 may determine an updated dosage or an updated timing for the delivery of the compounds. For example, the processor 206 may receive the subject's actual calorie intake for the day and compare it to the recommended calorie intake. The actual calorie intake may be higher than the recommended calorie intake, and the processor 206 may determine that the dosage of pyruvate is to be doubled to 12 g corresponding to 12 mL of pyruvate solution. The processor 206 may transmit the updated dosage to the second dispensing unit 216, and the second dispensing unit 216 may deliver 12 mL of the pyruvate solution at 3:00 AM based on the updated dosage. In another example, based on the updated information, the processor 206 may determine a second timing or a second dosage for the delivery of the compounds. A dispensing unit may then deliver the compounds based on the determined timing and dosage as well as the second determined timing and dosage. For example, based on the determination that the actual calorie intake is higher than the recommended calorie intake, the processor 206 may determine that 6 mL of pyruvate solution is to also be delivered at 12:00 AM in addition to a similar dose at 3:00 AM. The processor 206 may transmit the second timing and second dosage to the second dispensing unit 216, and the second dispensing unit 216 may deliver 6 mL of the pyruvate solution at 12:00 AM and 3:00 AM based on the determined timing and dosage and the second determined timing and dosage.

In some examples, the apparatus 202 may be configured to provide feedback to the subject. For example, recommendations on the type of food subject may consume such as a low glycemic index meal to prevent hunger at a time in the future or an immediate sugary snack to avoid imminent low blood sugar may be provided to the subject. The feedback may be provided visually through an integrated display (not shown), through an integrated speaker (not shown), or through a message transmitted to a computing device associated with the subject. The feedback may also include monitored health aspect levels, current dosage or timing information, etc.

The apparatus 202 may further comprise a power source 224. The power source 224 may be one of: a single-use battery, a rechargeable battery, or a replaceable battery, among other examples. The power source 224 may be connected to an external power source and recharged or may be recharged wirelessly. According to some examples, the power source 224 may be configured to generate power through kinetic energy harvesting, body heat conversion, or solar power. The processor 206 may be further configured to monitor a power level of the power source 224 and provide the power level to the subject. For example, the power source 224 may be a rechargeable battery that needs to be recharged. The processor 206 may provide the power level of the power source 224 to the communication module 208, and the communication module 208 may notify the subject that the power source needs to be recharged. In some embodiments, the processor 206 may provide the notification to the subject.

FIG. 3 includes an example dispensing apparatus that may be worn by a subject, arranged in accordance with at least some embodiments described herein.

As shown in diagram 300, an apparatus 302 may be worn by a subject. For example, the apparatus 302 may be attached to the subject with a strap 304. According to some embodiments, the apparatus 302 may be integrated into an item of clothing or an accessory. For example, an apparatus may be integrated into a watch, a bracelet, a ring, a necklace, a hat, a shirt, a jacket, a shoe, a pair of pants, or the like. In other embodiments, the apparatus 302 may be attached and removed from an article of clothing. For example, a subject may be enabled to attach the apparatus to a first shirt on a first day, remove the apparatus 302 from the first shirt, and attach the apparatus 302 to a second shirt the following day.

The apparatus 302 may comprise, a processor 306, a communication module 308, a first dispensing unit 310, a second dispensing unit 312, a third dispensing unit 314, a sensor 316, and a power source 318. The apparatus 302 may also be communicatively coupled to a display device 320. As discussed above in conjunction with FIG. 1 and FIG. 2, the processor 306 may receive information associated with a subject via the communication module 308. Based on the received information, the processor may determine a timing and a dosage for the delivery of compounds. For example, the processor 306 may receive, via the communication module 308, a current weight of the subject, a goal weight, a recommended calorie intake, an actual calorie intake, a recommended calorie expenditure, an actual calorie expenditure, a sleep schedule, a circadian rhythm of the subject, one or more average mealtimes for the subject, an average temperature based on the circadian rhythm, a BMR of the subject, or a metabolic rate based on the circadian rhythm. The processor 306 may then determine a dosage and a timing for the delivery for the compounds and instruct the first dispensing unit 310, the second dispensing unit 312, and the third dispensing unit 314 to deliver the compounds based on the determined dosages and timings.

The first dispensing unit 310, the second dispensing unit 312, and the third dispensing unit 314 may receive the determined dosages and timings from the processor 306. As shown in diagram 300, each dispensing unit may be coupled to more than one cartridge in order to store the compounds. In other embodiments, the cartridges may be separate components. In an example scenario, the cartridges coupled to the first dispensing unit 310 may store 3 different appetite suppressants; the cartridges coupled to the second dispensing unit 312 may store 3 different metabolic stimulators, and the cartridges coupled to the third dispensing unit 314 may store 3 different satiation compounds. The processor 306 may determine a dosage and timing for delivering each of the compounds. For example, the processor 306 may determine that 3 mL of a first satiation compound is to be delivered at an average breakfast time, such as 9:00 AM, 3 mL of a second satiation compound is to be delivered at an average lunch time, such as 1:00 PM, and 3 mL of a third satiation compound is to be delivered at an average dinner time, such as 7:00 PM. The third dispensing unit 314 may receive the determined dosages and timings and may deliver the satiation compounds onto the subject's skin 322 accordingly. The processor 306 may receive updated information associated with the subject and may determine an updated dosage or an updated timing for the delivery of the compounds. The dispensing units may then deliver the compounds based on the updated information associated with the subject.

The apparatus 302 may further comprise a sensor 316. The sensor 316 may include accelerometers to measure movement during wake and sleep cycles, audio sensors such as microphones, visual sensors such as cameras or light sensors, gyroscopes, and biometric sensors such as a thermometer, a heart rate monitor, an electrocardiogram, an electromyographic, or a blood pressure sensor. The sensor 316 may collect data associated with the subject and may transmit the data to the processor 306. The processor 306 may determine an updated dosage or timing for the delivery of the compounds based on the received data and may instruction the dispensing units to deliver the compounds, accordingly. For example, the sensor 316 may include a thermometer and may monitor the subject's temperature.

The sensor 316 may transmit data associated with the subject's temperature to the processor 306. The processor 306 may analyze the received data to determine the subject's BMR and may update a recommended calorie intake based on the determine BMR. The processor 306 may compare determined BMR to an initial BMR for the subject and may increase the recommended calorie intake. Accordingly, the subject may need to eat more, and the processor 306 may update the timings for the delivery of the satiation compounds to only include delivering the first satiation compound at 9:00 AM and the third satiation compound at 7:00 PM with the same dosages.

As discussed above, the apparatus 302 may be communicatively coupled to a display device 320, such as a monitor, a touch-enabled display, a television, or a virtual reality display. The processor 306 may be configured to generate a visualization of data associated with weight management to be presented to the subject. The visualization may include the information associated with the subject, the determined dosages or timings, an upcoming dose with a dosage and timing, or a last dose with a dosage and timing. The visualization may also include information that is based on updated information received by the processor 306. For example, the subject may enter the food they have eaten throughout the day, and the processor 306 may calculate an actual calorie intake. The processor 306 may then generate a visualization that includes a comparison of the actual calorie intake to the recommended calorie intake. The visualization may also provide comparisons of a current state of the subject to a goal. For example, the visualization may describe progress the subject has made and trends, such as projected amount of weight loss or gain per day, exercise patterns, eating habits, sleeping habits, or the like. The visualization may include data collected by the sensor 316. In an example scenario, the sensor 316 may include a pedometer and the visualization may include a number of steps taken. The visualization may also include information about components of the apparatus 302, such as a power level of the power source 318, a fill level of the cartridges, or a current time.

The processor 306 may be further configured to order or prioritize the information and data included in the visualization. The prioritization may be based on user inputs or interactions with the information or may be determined based on an analysis of the information associated with the subject. In a first example, the subject may regularly enter food they have eaten throughout the day and interact with elements of the visualization pertaining to caloric intake. The processor 306 may analyze these interactions and a representation of caloric intake first in the visualization. The representation may be graphical or textual. In another example, the sensor 316 may detect an awake state late at night, which may not be consistent with an optimal sleep schedule. The processor 306 may receive this information from the sensor 316 and may place information or a graphical representation that indicates a lack of sleep or a recommended bed time ahead of other information in the visualization based on the analysis.

The apparatus 302 may further comprise a power source 318. The power source 318 may be one of: a single-use battery, a rechargeable battery, or a replaceable battery, among other examples. The power source 318 may be connected to an external power source and recharged or may be recharged wirelessly. According to some examples, the power source 318 may be configured to generate power through kinetic energy harvesting, body heat conversion, or solar power.

Figure 4:
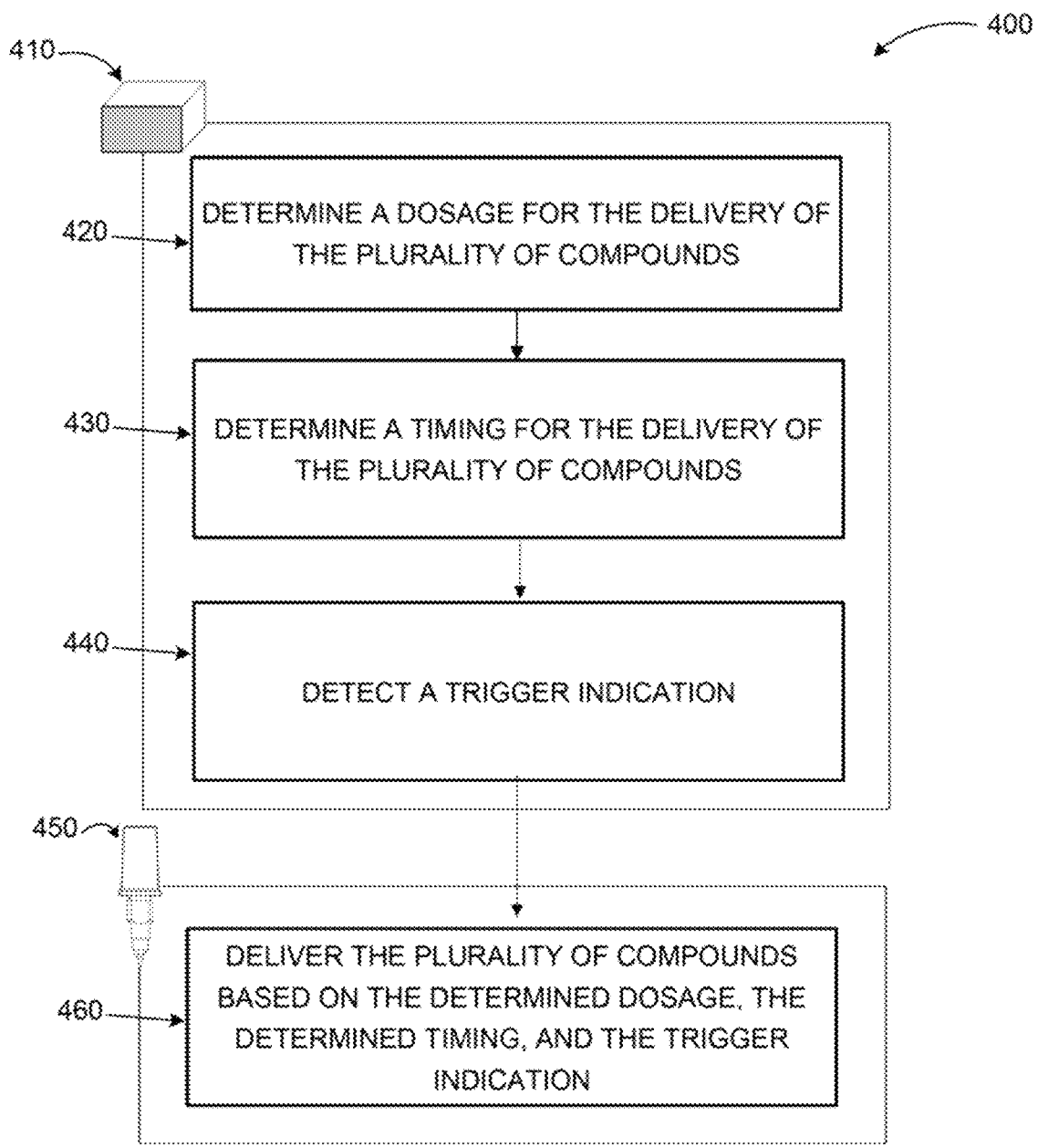
FIG. 4 includes a conceptual illustration of an example system configured to deliver compounds to aid in weight management.

FIG. 4 includes a flow diagram illustrating an example method to deliver compounds to aid in weight management and the components configured to execute the actions, arranged in accordance with at least some embodiments described herein.

As shown in diagram 400, a controller 410 may be configured to perform tasks associated with the delivery of the compounds to aid in weight management. The controller 410 may be a part of an apparatus, as shown in FIGS. 1, 2, and 3. First, the controller 410 may be configured to determine a dosage for the delivery of the plurality of compounds, as shown in block 420. The controller 410 may determine the dosage based on information associated with a subject. The information associated with the subject may be received from an external source, such as another computing device, or may be stored locally. For example, an apparatus that includes the controller 410 may also include a local storage. The controller 410 may analyze the information associated with the subject in order to determine a dosage for the individual delivery of the compounds. For example, the controller 410 may determine a dosage based on the subject's weight, a goal weight, a recommended calorie intake, an actual calorie intake, a recommended calorie expenditure, an actual calorie expenditure, a sleep schedule, a circadian rhythm of the subject, one or more average mealtimes for the subject, an average temperature based on the circadian rhythm, a BMR of the subject, or a metabolic rate based on the circadian rhythm. The controller 410 may also determine a timing for the delivery of the plurality of compounds as shown in block 430. The controller 410 may also determine the timing based on the analysis of the information associated with the subject.

The controller 410 may be further configured to detect a trigger indication as shown in block 440. The trigger indication may include detecting a current time and determining the current time matches a determined timing for the delivery of one or more of the compounds. The trigger indication may also be based on an input. For example, the controller 410 may receive updated information that includes an actual calorie intake, which may be substantially higher than a recommended calorie intake. Based on the updated information, the controller 410 may detect a trigger indication and may determine to immediately deliver a compound, such as a metabolic stimulator. In other examples, the trigger indication may include a manual input. For example, the controller 410 may be a component of an apparatus that includes means to receive a manual input, such as a button, a switch, a touch screen, a gesture capture device, or the like. The subject may enter an input indicating hunger after a meal. The controller 410 may receive the input, detect a trigger indication based on the input, and may determine to immediately deliver a compound, such as a satiation compound based on the input and detected trigger indication.

Moreover, a dispensing unit 450 may be configured to deliver the compounds based on the determined dosage, the determined timing, and the trigger indication. The dispensing unit 450 may receive the determined dosage, the determined timing, and the trigger indication from the controller 410 and may deliver the compounds. In some examples, the controller 410 may instruct the dispensing unit 450 to deliver the compounds based on determined dosage, the determined timing, and the trigger indication. The dispensing unit 450 may deliver the compounds directly onto the skin of the subject or onto a wicking layer that is in contact with the skin (460), according to some examples. The dispensing unit 450 may be a Joule-heating dispenser or a piezoelectric dispenser and may measure the volume of each compound delivered to the subject such that the correct dosage is applied.

In some examples, a device or system according to embodiments may be used to treat conditions such as for type 2 Diabetes mellitus (DM) and preconditions such as metabolic disorder as part of an overall weight management program. For specific management of DM, blood sugar measurements may be integrated over time to determine whether the program that the system is administering is effective for the patient to manage their blood sugar levels throughout the day and from day to day. If there are abnormal elevations in blood sugar at a particular time, the system may modify treatment towards weight loss (e.g., increase appetite suppression, increase metabolic stimulation, and/or increase satiation dose schedules). If there are abnormal decreases in blood sugars, the system may work to reduce one or more of these levels.

Figure 5:
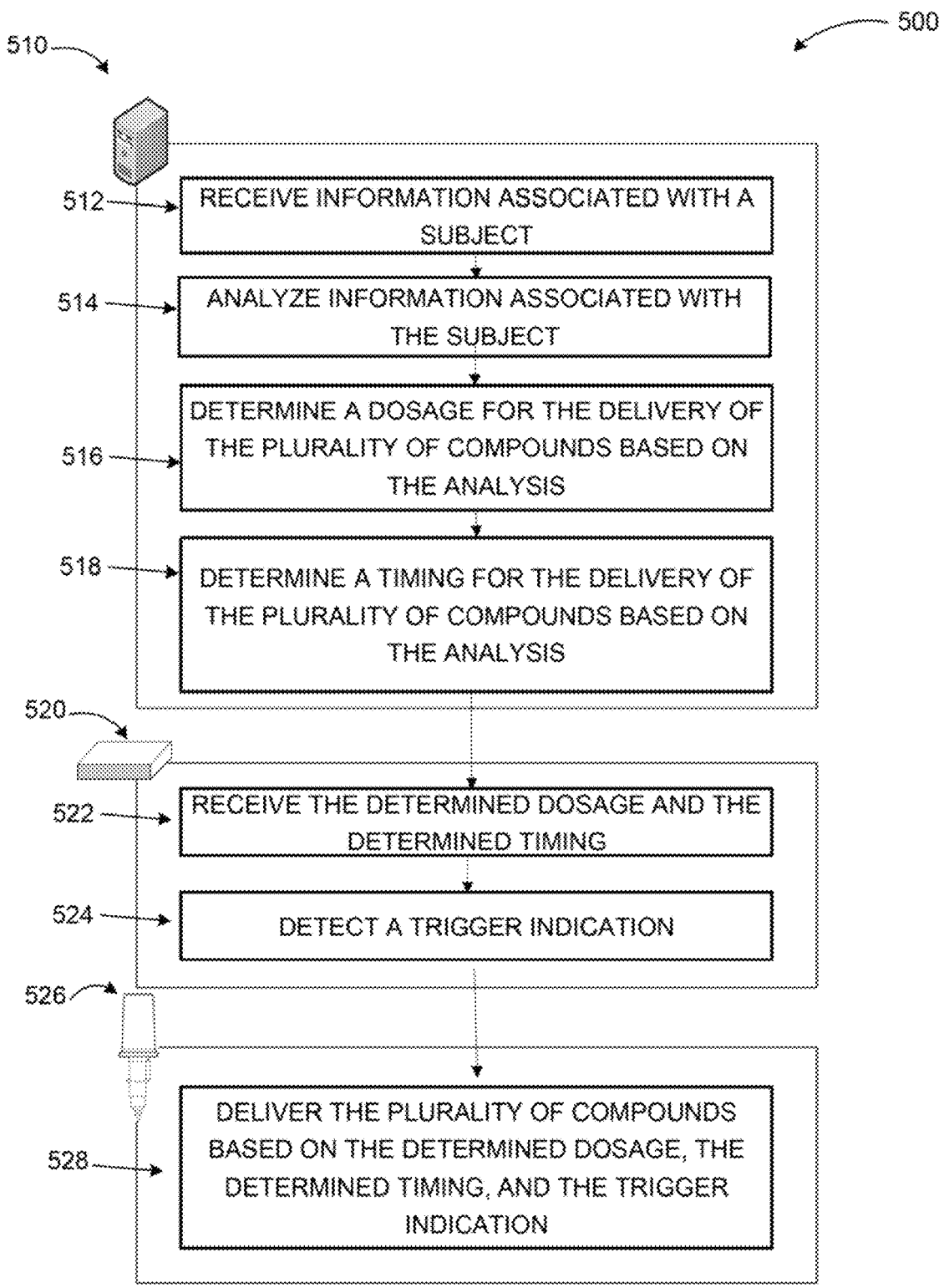
FIG. 5 includes a flow diagram illustrating an example method to deliver compounds to aid in weight management and the components configured to execute the actions.

FIG. 5 includes a flow diagram illustrating another example method to deliver compounds to aid in weight management based on received data and the components configured to execute the actions, arranged in accordance with at least some embodiments described herein.

As shown in diagram 500, a computing device 510 (e.g., a server, a desktop computer, a mobile computer, a special purpose computing device, a laptop, a smart phone, or even a component level processor) may be configured to receive information associated with a subject, as described in the previous figures and shown in block 512. The computing device 510 may also include a database configured to store a health record of the subject as well as one or more health factors. The health factors may include one or more vital signs, a body mass index, any pre-existing conditions, any medications the subject is currently prescribed, and a medical history of the subject. In some examples, the one or more health factors may be stored in an external database that the computing device 510 may be communicatively coupled to.

The computing device 510 may also be configured to analyze the information associated with the subject as shown in block 514. For example, the computing device 510 may compare current values to goal values, such as a current weight and a goal weight or an actual calorie intake vs. a recommended calorie intake. The computing device 510 may analyze the information associated with the subject as well as the one or more health factors to determine one or more compounds to deliver to the person. The determination may be made to optimize the efficacy of the compounds delivered to the subject. For example, the subject may wish to lose 40 kg of body weight and another subject may wish to only lose 5 kg of body weight. The computing device 510 may select different compounds for each subject based on their goals, medical histories, of information associated with each subject. Based on the analysis, the computing device 510 may determine a timing and a dosage for the delivery of the plurality of compounds as shown in blocks 516 and 518. The computing device 510 may then transmit the determined timings and dosages to a processor 520.

The processor 520 may be a controller according to some examples. The processor 520 may configured to receive the determined dosages and timings (522) from the computing device 510. For example, the processor 520 may be receive the determined dosages and timings via a network according to some embodiments. The processor 520 may also be configured to detect a trigger indication as shown in block 524. The dispensing unit 526 may then deliver the compounds based on the determined dosage, the determined timing, and the detected trigger indication (528).

Figure 6:
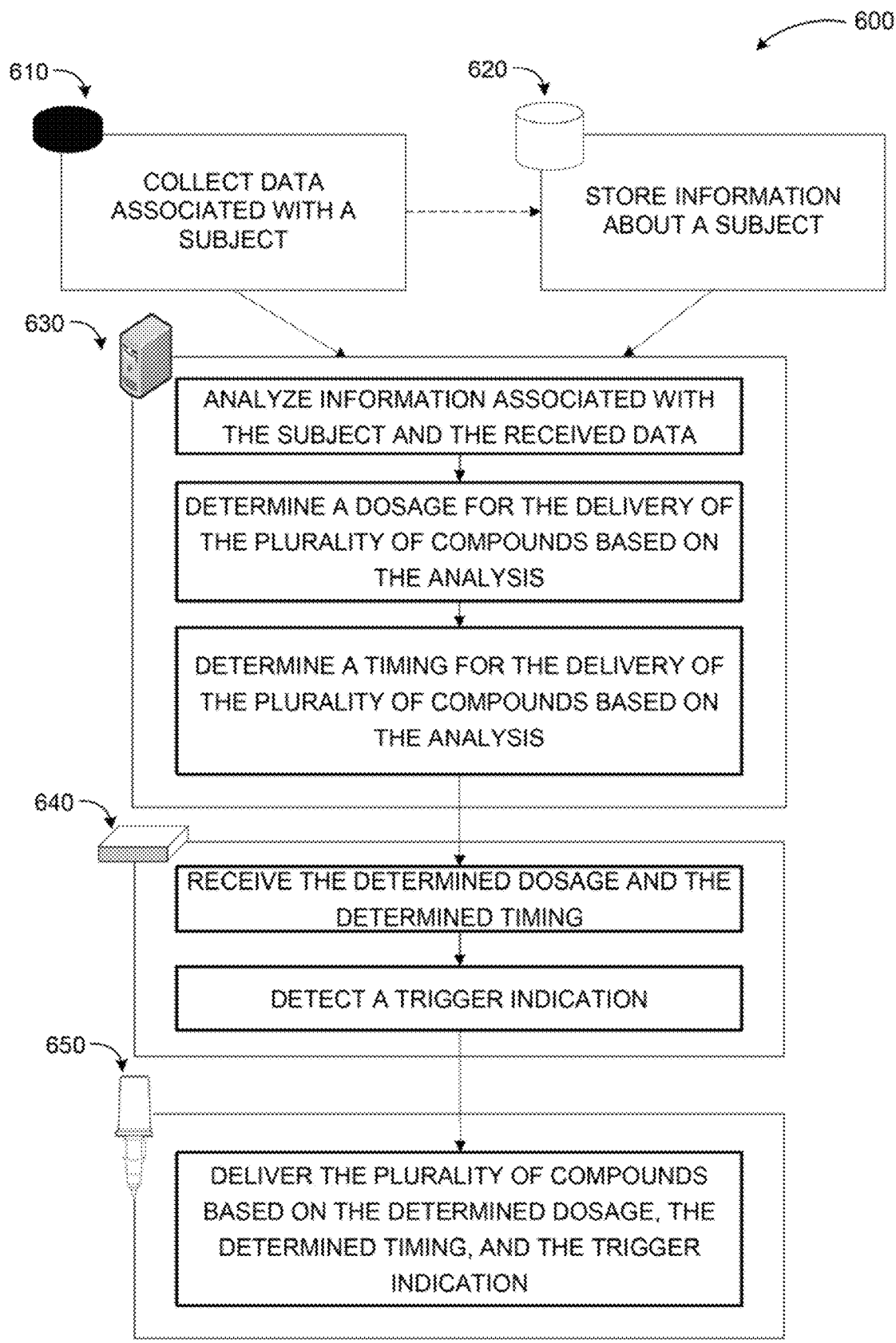
FIG. 6 includes a flow diagram illustrating another example method to deliver compounds to aid in weight management based on received data and the components configured to execute the actions.

FIG. 6 includes a flow diagram illustrating another example method to collect and store information associated with a subject in order to deliver compounds to aid in weight management based on received data and the components configured to execute the actions, arranged in accordance with at least some embodiments described herein.

As shown in diagram 600, one or more sensors 610 may be configured to collect data associated with a subject. The one or more sensors 610 may include accelerometers, audio sensors such as microphones, visual sensors such as cameras or light sensors, gyroscopes, and biometric sensors such as a thermometer, a heart rate monitor, an electrocardiogram, an electromyographic, or a blood pressure sensor. The one or more sensors 610 may transmit the collected data to a data store 620. The data store 620 may store the collected information as well as other information associated with the subject. The one or more sensors 610 and the data store 620 may transmit the collected information and the stored information, respectively, to the computing device 630.

The computing device 630 may receive the information associated with the subject and analyze the information to determine dosages and timings for the delivery of the compounds. The one or more sensors 610 may continuously or periodically transmit collected information to the computing device 630, and the computing device 630 may update the dosages or timings based on the received data. For example, the one or more sensors 610 may include an accelerometer that measure's the subject's activity and may transmit information associated with the subject's activity to the computing device 630. The computing device 630 may determine a low level of activity during an afternoon and may determine to increase a dosage of a metabolic stimulator based on the determination.

The computing device 630 may transmit the determined timings and dosages to a processor 640, which may be a controller according to some embodiments. The processor 640 may receive the determined dosages and timings from the computing device 630. The processor 640 may also detect a trigger indication and may transmit the determined dosages and timings as well as the trigger indication to the dispensing unit 650. The dispensing unit 650 may deliver the compounds based on the determined dosages, the determined timings, and the trigger indication. Returning to the example in the paragraph above, the processor 640 may receive the updated dosage for the metabolic stimulator and may detect a trigger indication. The processor 640 may transmit the determined timing, the updated dosage, and the trigger indication to the dispensing unit 650. The dispensing unit 650 may deliver the metabolic stimulator based on the determined timing, the updated dosage, and the trigger indication.

Figure 7:
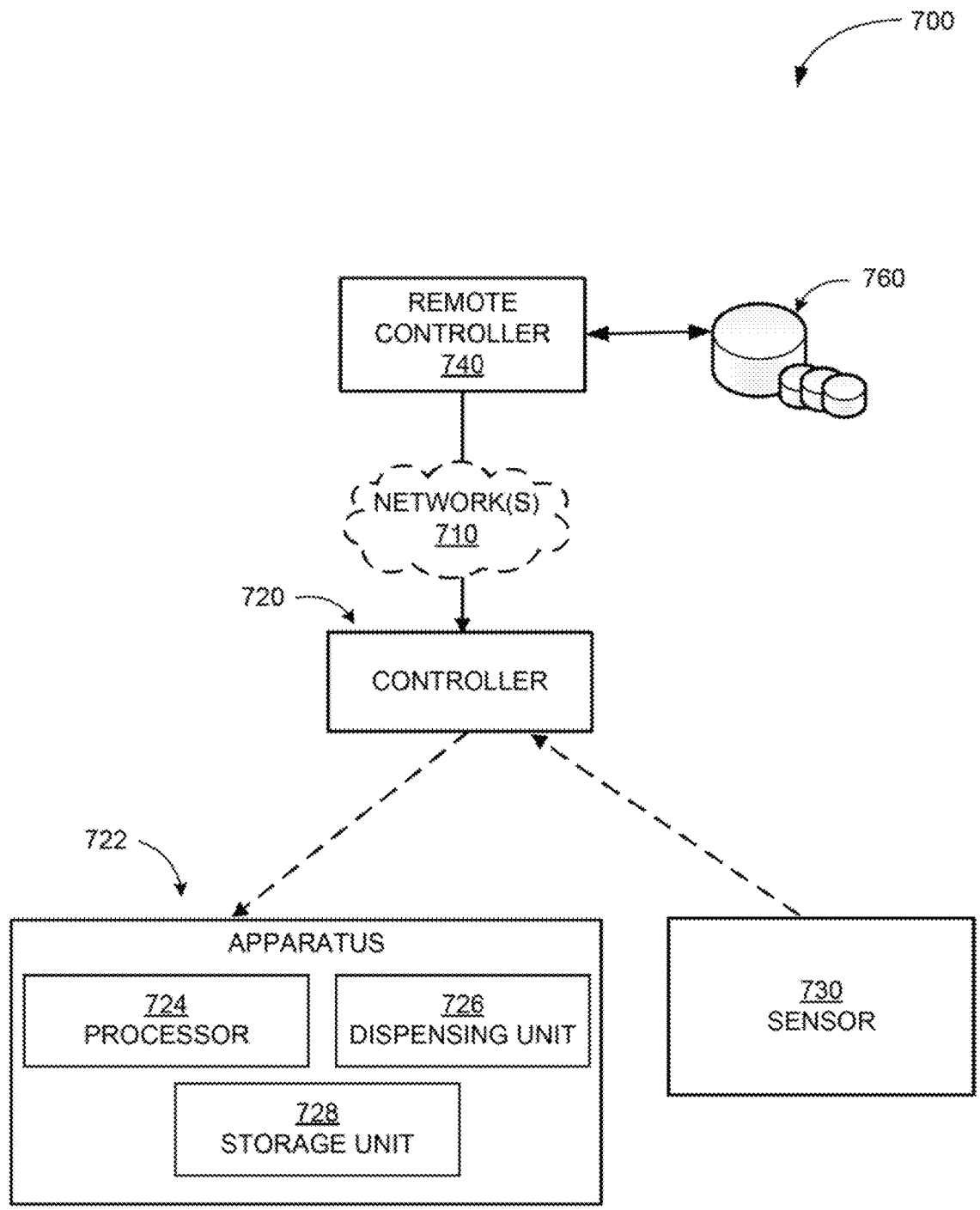
FIG. 7 includes a flow diagram illustrating another example method to collect and store information associated with a subject in order to deliver compounds to aid in weight management based on received data and the components configured to execute the actions.

FIG. 7 includes a conceptual illustration of an example system configured to deliver compounds to aid in weight management, arranged in accordance with at least some embodiments described herein.

As shown in diagram 700, an apparatus 722 and a sensor 730 may be governed by a system controller 720. The processor 730 may be a controller, such as the processor 106, 206, or 306 as described in conjunction with FIGS. 1, 2, and 3, for example. The system controller 720 may be managed manually through a variety of inputs, may operate automatically after receiving one or more instructions, or may be operated independently by software. The system controller 720 may also be partially or entirely managed by a remote controller 740, for example, via network 710. The remote controller 740 may be managed manually through a variety of inputs, may operate automatically after receiving one or more instructions, or may be operated independently by software. Data associated with controlling the different processes of delivering compounds to aid in weight management may be stored at and/or received from data stores 760.

The apparatus 722 may include a processor 724, a dispensing unit 726, and a storage unit 728 in accordance with other embodiments described herein. The processor 724 may be configured to receive information associated with a subject, as described above. The processor 724 may periodically receive updated information from the controller 720 and, according to some embodiments, may receive a protocol for the delivery of compounds. The protocol may include one or more pre-determined timings or one or more pre-determined dosages. In some examples, the processor 724 may analyze the received information and may determine a timing and a dosage for the delivery of the compounds. The processor 724 may be further configured to detect a trigger indication. The processor 724 may transmit the determined timings, determined dosages, and the detected trigger indication, to the dispensing unit 726. The dispensing unit 726 may be a single dispenser or an array of dispensers and may include one or more Joule-heating dispensers and/or one or more piezoelectric dispensers. The dispensing unit 726 may be coupled to or connected to the storage unit 728. The storage unit 728 may include one or more cartridges. The one or more cartridges may be refillable or replaceable and may store the compounds. The dispensing unit 726 may deliver the compounds based on the determined timings, determined dosages, and the detected trigger indication. The dispensing unit 726 may deliver the compounds onto the skin of the subject or onto a wicking layer that is in contact with the skin.

The sensor 730 may be configured to collect data associated with the subject. In some embodiments, the sensor 730 may be integrated with the apparatus 722. The sensor 730 may also be integrated into another computing device such as a mobile device or a fitness product. The sensor 730 may transmit the collected data to the controller 720, and the controller 720 may update the information associated with the subject based on the collected data. The controller 720 may provide the collected data to the processor 724, which may update the dosages or timings for the delivery of the compounds based on the collected data. In some examples, the controller 720 may update the protocol for the delivery of the compounds based on the collected data. The controller 720 may transmit the updated protocol to the processor 724, and the dispensing unit 726 may deliver the compounds based on the updated protocol. Furthermore, the controller 720 may update the information stored in the data stores 760 based on the collected data.

The examples provided in FIGS. 1 through 7 are illustrated with specific systems, devices, and processes. Embodiments are not limited to environments according to these examples. Situationally tailored control and optimization of delivery of compounds to aid in weight management may be implemented in environments employing fewer or additional systems, devices, and processes. Furthermore, the example systems, devices, and processes shown in FIGS. 1 through 7 may be implemented in a similar manner with other values using the principles described herein.

Figure 8:
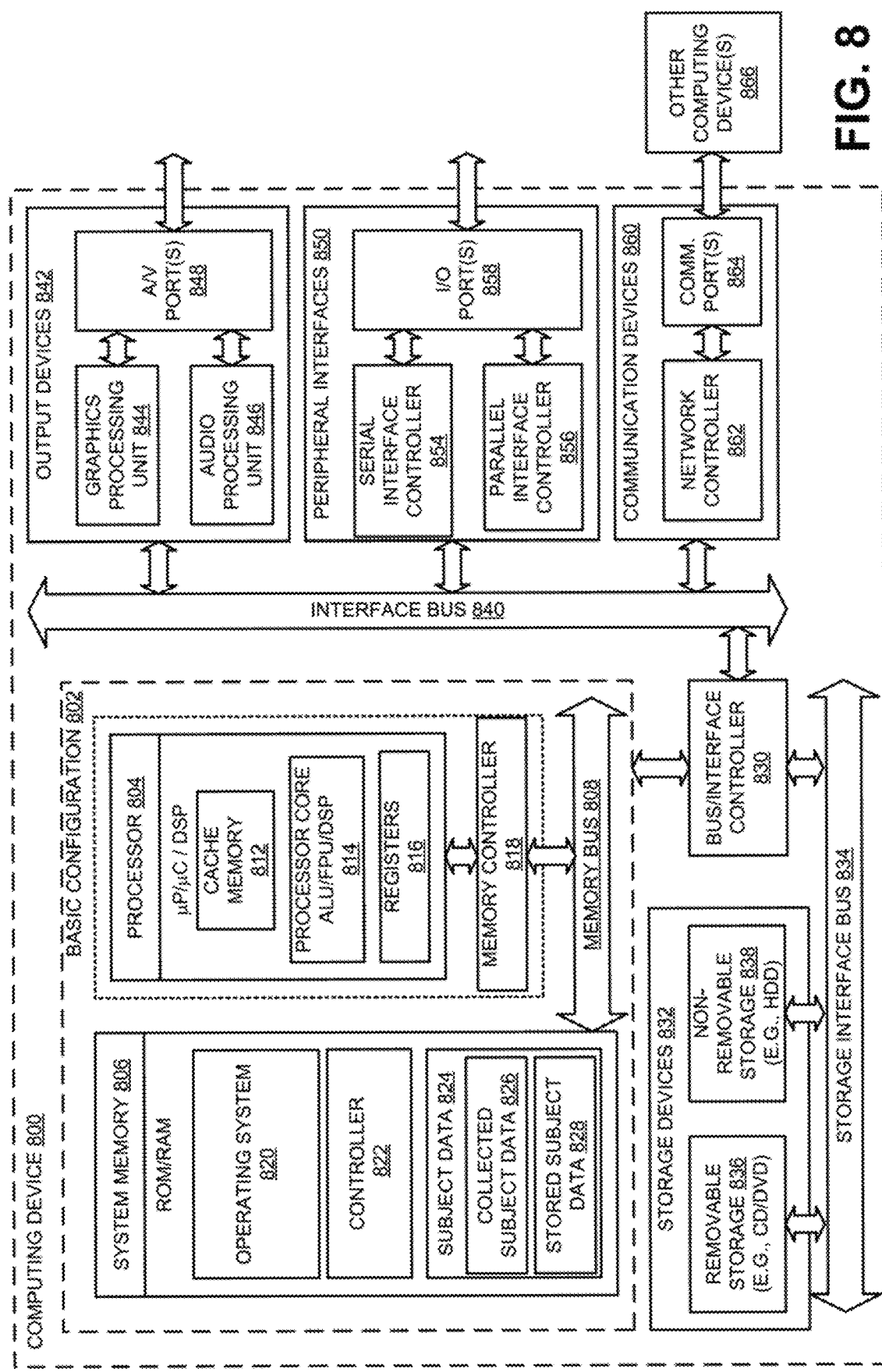
FIG. 8 illustrates a computing device, which may be used to perform delivery of compounds to aid in weight management.

FIG. 8 illustrates a computing device, which may be used to perform delivery of compounds to aid in weight management, arranged in accordance with at least some embodiments described herein.

In an example basic configuration 802, the computing device 800 may include one or more processors 804 and a system memory 806. A memory bus 808 may be used to communicate between the processor 804 and the system memory 806. The basic configuration 802 is illustrated in FIG. 8 by those components within the inner dashed line.

Depending on the desired configuration, the processor 804 may be of any type, including but not limited to a microprocessor (μP), a microcontroller (μC), a digital signal processor (DSP), or any combination thereof. The processor 804 may include one or more levels of caching, such as a cache memory 812, a processor core 814, and registers 816. The example processor core 814 may include an arithmetic logic unit (ALU), a floating point unit (FPU), a digital signal processing core (DSP Core), or any combination thereof. An example memory controller 818 may also be used with the processor 804, or in some implementations, the memory controller 818 may be an internal part of the processor 804.

Depending on the desired configuration, the system memory 806 may be of any type including but not limited to volatile memory (such as RAM), non-volatile memory (such as ROM, flash memory, etc.) or any combination thereof. The system memory 806 may include an operating system 820, a controller 822, and program data 824. The controller 822 may receive information associated with a subject, determine a timing for the delivery of compounds, and determine a dosage for the delivery of the compounds. The controller 822 may also detect a trigger indication and transmit the determined timing, determined dosage, and the detected trigger indication to a dispensing unit or an apparatus for the delivery of the plurality plurality of compounds. The controller 822 may also receive updated information associated with the subject and update the timing or dosage based on the updated information. The controller 822 may also be configured to receive collected data associated with the subject from one or more sensors. The controller 822 may store the information associated with the subject as well as the collected data in the program data 824. Program data 824 may include collected subject data 826 and stored subject data 828. The collected subject data 826 and the stored subject data 828 may be received from the controller 822 or may be received from another computing device.

The computing device 800 may have additional features or functionality, and additional interfaces to facilitate communications between the basic configuration 802 and any desired devices and interfaces. For example, a bus/interface controller 830 may be used to facilitate communications between the basic configuration 802 and one or more data storage devices 832 via a storage interface bus 834. The data storage devices 832 may be one or more removable storage devices 836, one or more non-removable storage devices 838, or a combination thereof. Examples of the removable storage and the non-removable storage devices include magnetic disk devices such as flexible disk drives and hard-disk drives (HDDs), optical disk drives such as compact disc (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer readable instructions, data structures, program modules, or other data.

The system memory 806, the removable storage devices 836 and the non-removable storage devices 838 are examples of computer storage media. Computer storage media includes, but is not limited to, RAM, ROM, EEPROM, flash memory or other memory technology, CD-ROM, digital versatile disks (DVDs), solid state drives, or other optical storage, magnetic cassettes, magnetic tape, magnetic disk storage or other magnetic storage devices, or any other medium which may be used to store the desired information and which may be accessed by the computing device 800. Any such computer storage media may be part of the computing device 800.

The computing device 800 may also include an interface bus 840 for facilitating communication from various interface devices (e.g., one or more output devices 842, one or more peripheral interfaces 850, and one or more communication devices 860) to the basic configuration 802 via the bus/interface controller 840. Some of the example output devices 842 include a graphics processing unit 844 and an audio processing unit 846, which may be configured to communicate to various external devices such as a display or speakers via one or more A/V ports 848. One or more example peripheral interfaces 850 may include a serial interface controller 854 or a parallel interface controller 856, which may be configured to communicate with external devices such as input devices (e.g., keyboard, mouse, pen, voice input device, touch input device, etc.) or other peripheral devices (e.g., printer, scanner, etc.) via one or more I/O ports 858. An example communication device 860 includes a network controller 862, which may be arranged to facilitate communications with one or more other computing devices 866 over a network communication link via one or more communication ports 864. The one or more other computing devices 866 may include servers at a datacenter, customer equipment, and comparable devices.

The network communication link may be one example of a communication media. Communication media may be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 800 may be implemented as a part of a general purpose or specialized server, mainframe, or similar computer that includes any of the above functions. The computing device 800 may also be implemented as a personal computer including both laptop computer and non-laptop computer configurations.

Figure 9:
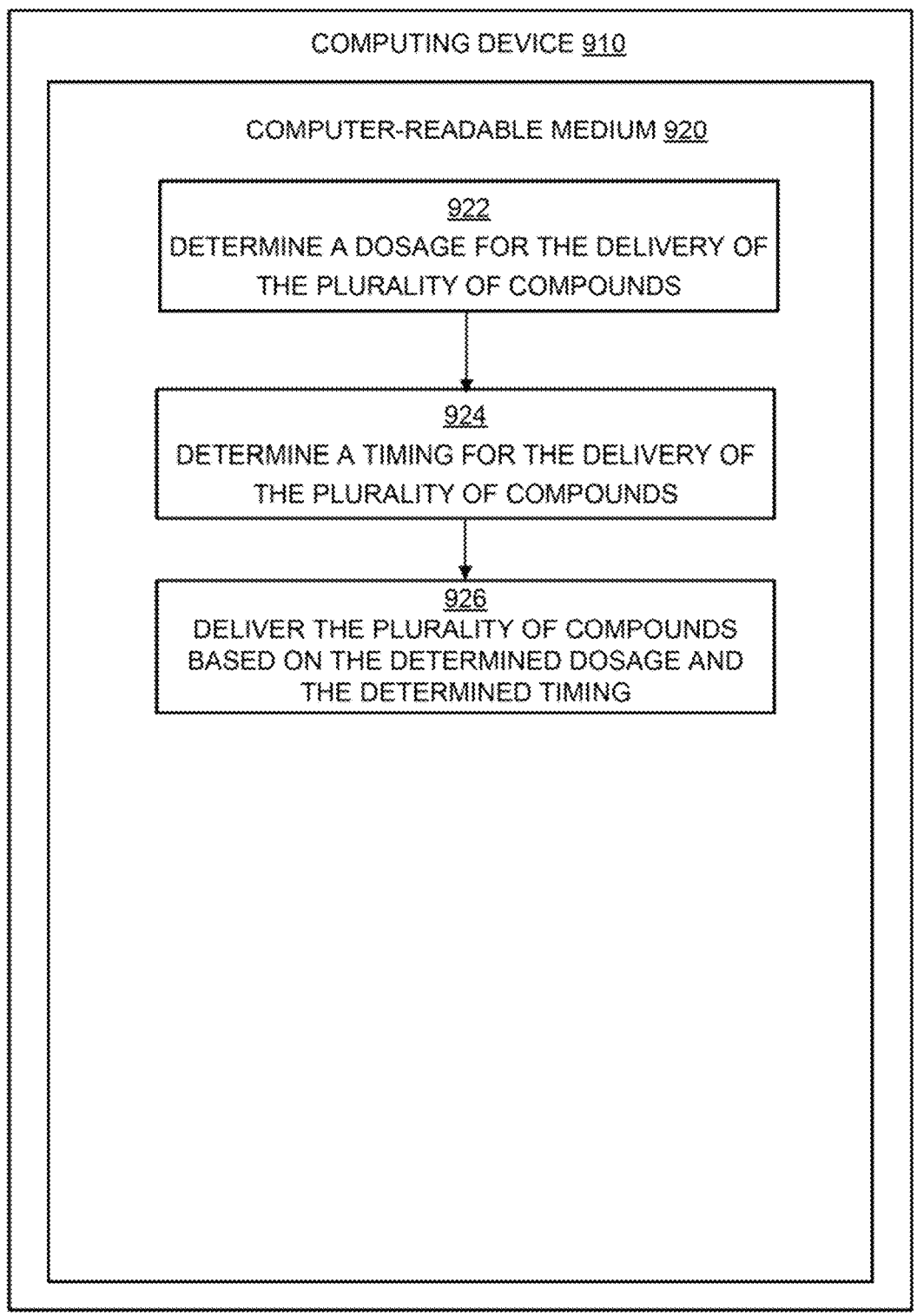
FIG. 9 is a flow diagram illustrating an example method to analyze a liquid sample that may be performed by a computing device.

FIG. 9 is a flow diagram illustrating an example method to analyze a liquid sample that may be performed by a computing device such as the computing device in FIG. 8. Example methods may include one or more operations, functions or actions as illustrated by one or more of blocks 922, 924, and 926, and may in some embodiments be performed by a computing device such as the computing device 800 in FIG. 8. The operations described in the blocks 922, 924, and 926 may also be stored as computer-executable instructions in a computer-readable medium such as a computer-readable medium 920 of a computing device 910.

An example process to analyze a liquid sample may begin with block 922, "DETERMINE A DOSAGE FOR THE DELIVERY OF THE PLURALITY OF COMPOUNDS", where a processor, which may be a controller, may determine a dosage for each compound based on information associated with a subject. For example, the information associated with the subject may include the subject's current weight and the processor may determine the dosage based on the subject's current weight.

Block 922 may be followed by block 924, "DETERMINE A TIMING FOR THE DELIVERY OF THE PLURALITY OF COMPOUNDS", where the processor may determine a timing for each compound based on the information associated with the subject and the type of compound being delivered. For example, an appetite suppressant may be delivered following a meal. The information associated with the subject may include average mealtimes for the subject, and the processor may determine a timing for the delivery of an appetite suppressant based on the average mealtimes. In another example, a satiation compound may be delivered at a mealtime, and the processor may also determine the timing for the delivery of the satiation compound based on the average mealtimes for the subject. Furthermore, a metabolic stimulator may be delivered based on a comparison of an actual calorie intake and a recommended calorie intake. The processor may compare the actual calorie intake and the recommended calorie intake to determine that the metabolic stimulator may be delivered following the subject consuming a large lunch that exceeds the recommended calorie intake.

Block 924 may be followed by block 926, "DELIVER THE PLURALITY OF COMPOUNDS BASED ON THE DETERMINED DOSAGE AND THE DETERMINED TIMING", where a dispensing unit may receive the determined dosage and the determined timing for the delivery of the compounds from the processor. The dispensing unit may then deliver the compounds based on the determined dosage and the determined timing. In some examples, the dispensing unit may also deliver the compounds based on a detected trigger indication.

FIG. 10 illustrates a block diagram of an example computer program product, some of which are arranged in accordance with at least some embodiments described herein.

In some examples, as shown in FIG. 10, a computer program product 1000 may include a signal-bearing medium 1002 that may also include one or more machine readable instructions 804 that, when executed by, for example, a processor may provide the functionality described herein. Thus, for example, referring to the processor 804 in FIG. 8, the controller 822 may undertake one or more of the tasks shown in FIG. 10 in response to the instructions 1004 conveyed to the processor 804 by the signal-bearing medium 1002 to perform actions associated with analyzing a liquid sample as described herein. Some of those instructions may include, for example, instructions to determine a dosage for the delivery of the compounds, determine a timing for the delivery of the compounds, and deliver the compounds based on the determined dosage and the determined timing, according to some embodiments described herein.

In some implementations, the signal-bearing medium 1002 depicted in FIG. 10 may encompass computer-readable medium 1006, such as, but not limited to, a hard disk drive, a solid state drive, a Compact Disc (CD), a Digital Versatile Disk (DVD), a digital tape, memory, etc. In some implementations, the signal-bearing medium 1002 may encompass recordable medium 1008, such as, but not limited to, memory, read/write (R/W) CDs, R/W DVDs, etc. In some implementations, the signal-bearing medium 1002 may encompass communications medium 1010, such as, but not limited to, a digital and/or an analog communication medium (for example, a fiber optic cable, a waveguide, a wired communications link, a wireless communication link, etc.). Thus, for example, the computer program product 1000 may be conveyed to one or more modules of the processor 804 by an RF signal bearing medium, where the signal-bearing medium 1002 is conveyed by a communications medium 1010 (for example, a wireless communications medium conforming with the IEEE 802.11 standard).

According to some examples, a transdermal dispensing apparatus for a delivery of a plurality of compounds to aid in weight management may be described. The apparatus may include a processor configured to determine a dosage for individual delivery of the plurality of compounds and determine a timing for the individual delivery of the plurality of compounds. The apparatus may also include a dispensing unit communicatively coupled to the processor and configured to deliver the plurality of compounds transdermally based on the determined dosage and the determined timing.

According to other examples, the apparatus may be worn on skin or attached to an area of the skin with an adhesive layer. The plurality of compounds may include an appetite suppressant, a metabolic stimulator, and a satiating compound. The appetite suppressant may include diethylpropion, oxymetazoline, phentermine, rimonabant, sibutramine, bitter orange, chromium, forskolin, hydroxycitric acid, glucomannan, guar gum, or hoodia. The appetite suppressant may be delivered between mealtimes. The metabolic stimulator may include caffeine, bitter orange, calcium, chromium, conjugated linoleic acid, fucoxanthin, green coffee bean extract, pyruvate, raspberry ketone, white kidney bean, yohimbe, L-Tyrosine, L-Carnitine, green tea, resveratrol, nootkatone, or capsaicin. The metabolic stimulator may be delivered based on a comparison of an actual calorie intake and a recommended calorie intake. The satiating compound may include cholecystokinin, glucagon-like peptide 1, peptide YY, oxyntomodulin, apolipoprotein A-IV, enterostatin, bombesin-family peptides such as gastrin-releasing peptide and neuromedin B, amylin, leptin, glucomannan, guar gum, or chitosan. The satiating compound may be delivered during a mealtime.

According to further examples, the processor may be further configured to receive one or more of the dosage or the timing from a computing device communicatively coupled to the apparatus. The dispensing unit may be further configured to in response to receipt of the one or more of the dosage or the timing by the processor, deliver the plurality of compounds based on the one or more of the received dosage or the received timing. The processor may be further configured to receive a manual input and instruct the dispensing unit to deliver the plurality of compounds based on the manual input. The processor may also be configured to update one or more of the dosage or the timing based on the manual input. The apparatus may further include a storage unit for the plurality of compounds. The storage unit may include one or more cartridges for each of the plurality of compounds. The dispensing unit may include one or more dispensers coupled to corresponding one or more cartridges. The dispensing unit may also include a single dispenser coupled to the one or more cartridges. The one or more cartridges may be refillable or replaceable.

According to some examples, the dispensing unit may include an array of dispensers. The dispensing unit may include a piezo-electric dispenser or a Joule heating dispenser. The dispensing unit may be further configured to dispense the plurality of compounds directly onto skin. The dispensing unit may be further configured to dispense the plurality of compounds to a wicking layer that may be in contact with skin. The dispensing unit may also be configured to measure a volume of each delivered compound to determine a delivered dosage. The apparatus may also include a power source. The power source may be a single-use battery, a rechargeable battery, or a replaceable battery. The power source may be configured to generate power through kinetic energy harvesting, body heat conversion, or solar power. The apparatus may further include a display device. The display device may be configured to display data associated with the delivery of the plurality of compounds. Data associated with the delivery of the plurality of compounds may include one or more of the dosage for the delivery of the plurality of compounds, the timing for the delivery of the plurality of compounds, a current time, a fill-status of a storage unit, or a charge of a power source. The apparatus may also include one or more sensors. The one or more sensors may include an accelerometer, a heart rate sensor, a thermometer, or a blood pressure sensor.

According to other examples, a system for a delivery of a plurality of compounds to aid in weight management is described. The system may include a controller configured to analyze information associated with a subject; determine a dosage for individual delivery of the plurality of compounds based on the analysis; and determine a timing for the individual delivery of the plurality of compounds based on the analysis. The system may also include a delivery apparatus that may include a storage unit; a processor configured to receive the determined dosage and the determined timing from the controller; and a dispensing unit configured to deliver the plurality of compounds transdermally based on the determined dosage and the determined timing.

According to further examples, the apparatus may be worn on skin or attached to an area of the skin with an adhesive layer. Information associated with the subject may include a current weight, a goal weight, one or more average mealtimes, a sleep schedule, an actual calorie intake, a recommended calorie intake, and calories burned. The plurality of compounds may include an appetite suppressant, a metabolic stimulator, and a satiating compound. The appetite suppressant may include diethylpropion, oxymetazoline, phentermine, rimonabant, sibutramine, bitter orange, chromium, forskolin, hydroxycitric acid, glucomannan, guar gum, or hoodia. The appetite suppressant may be delivered between mealtimes. The metabolic stimulator may include caffeine, bitter orange, calcium, chromium, conjugated linoleic acid, fucoxanthin, green coffee bean extract, pyruvate, raspberry ketone, white kidney bean, yohimbe, L-Tyrosine, L-Carnitine, green tea, resveratrol, nootkatone, or capsaicin. The metabolic stimulator may be delivered based on a comparison of a daily calorie intake and a recommended daily calorie intake. The satiating compound may include cholecystokinin, glucagon-like peptide 1, peptide YY, oxyntomodulin, apolipoprotein A-IV, enterostatin, bombesin-family peptides such as gastrin-releasing peptide and neuromedin B, amylin, leptin, glucomannan, guar gum, or chitosan. The satiating compound may be delivered during a mealtime.

According to some examples, the controller may be further configured to receive an updated information associated with the subject; analyze the updated information associated with the subject; and determine an updated dosage and an updated timing for individual delivery of the plurality of compounds based on the analysis. The controller may be further configured to receive a delivery protocol, where the delivery protocol may include one or more pre-determined dosages and one or more pre-determined timings; and determine the dosage and the timing based on the one or more pre-determined dosages and the one or more pre-determined timings. The processor may be further configured to receive a manual input; and instruct the dispensing unit to deliver the plurality of compounds based on the manual input. The processor may be further configured to transmit the manual input to the controller. The controller may be further configured to update the information associated with the subject based on the manual input.

According to other examples, the system may further include one or more sensors. The one or more sensors may be an accelerometer, a heart rate sensor, a thermometer, or a blood pressure sensor. The controller may be further configured to receive an input from the one or more sensors; update the information associated with the subject based on the input from the one or more sensors; analyze the updated information associated with the subject; and determine an updated dosage and an updated timing for individual delivery of the plurality of compounds based on the analysis. The storage unit may include one or more cartridges for each of the plurality of compounds. The dispensing unit may include one or more dispensers coupled to corresponding one or more cartridges. The dispensing unit may include a single dispenser coupled to the one or more cartridges. The one or more cartridges may be refillable or replaceable. The dispensing unit may include an array of dispensers. The dispensing unit may include a piezo-electric dispenser or a Joule heating dispenser. The dispensing unit may be further configured to dispense the plurality of compounds directly onto skin. The dispensing unit may be further configured to dispense the plurality of compounds to a wicking layer that may be in contact with skin. The system may further include a display device. The display device may be configured to display data associated with the delivery of the plurality of compounds. Data associated with the delivery of the plurality of compounds may include one or more of the dosage for the delivery of the plurality of compounds, the timing for the delivery of the plurality of compounds, a current time, a fill-status of a storage unit, or a charge of a power source.

According to further examples, a method for a delivery of a plurality of compounds to aid in weight management is described. The method may include receiving the plurality of compounds; determining a dosage for individual delivery of the plurality of compounds; determining a timing for the individual delivery of the plurality of compounds; and delivering the plurality of compounds transdermally based on the determined dosage and the determined timing.

According to some examples, determining the dosage for individual delivery of the plurality of compounds may include analyzing information associated with a subject; and determining the dosage for individual delivery of the plurality of compounds based on the analysis. Information associated with the subject may include a current weight, a goal weight, one or more average mealtimes, a sleep schedule, an actual calorie intake, a recommended calorie intake, and calories burned. Determining the timing for the individual delivery of the plurality of compounds may include analyzing information associated with a subject; and determining the timing for individual delivery of the plurality of compounds based on the analysis. The method may further include receiving one or more pre-determined dosages and one or more pre-determined timings; and determining the dosage and the timing based on the pre-determined dosages and pre-determined timings.

According to other examples, delivering the plurality of compounds transdermally based on the determined dosage and the determined timing may include dispensing the plurality of compounds directly onto skin. Delivering the plurality of compounds transdermally based on the determined dosage and the determined timing may include dispensing the plurality of compounds to a wicking layer that may be in contact with skin. Receiving the plurality of compounds may include storing the plurality of compounds in one or more cartridges. The method may also include receiving an input; and delivering the plurality of compounds based on the input. The method may further include extracting data from the input; and updating the dosage and the timing based on the extracted data. The method may also include displaying data associated with the delivery of the plurality of compounds. The data associated with the delivery of the plurality of compounds may include one or more of the dosage for the delivery of the plurality of compounds, the timing for the delivery of the plurality of compounds, a current time, a fill-status of a storage unit, or a charge of a power source.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, may be equivalently implemented in integrated circuits, as one or more computer programs executing on one or more computers (e.g., as one or more programs executing on one or more computer systems), as one or more programs executing on one or more processors (e.g., as one or more programs executing on one or more microprocessors), as firmware, or as virtually any combination thereof, and designing the circuitry and/or writing the code for the software and/or firmware would be possible in light of this disclosure.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In addition, the mechanisms of the subject matter described herein are capable of being distributed as a program product in a variety of forms, and an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a compact disc (CD), a digital versatile disk (DVD), a digital tape, a computer memory, a solid state drive (SSD), etc.; and a transmission type medium such as a digital and/or an analog communication medium (e.g., a fiber optic cable, a waveguide, a wired communication link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. A data processing system may include one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors.

A data processing system may be implemented utilizing any suitable commercially available components, such as those found in data computing/communication and/or network computing/communication systems. The herein described subject matter sometimes illustrates different components contained within, or connected with, different other components. Such depicted architectures are merely exemplary, and in fact, many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no, such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments are possible. The various aspects and embodiments disclosed herein are for purposes of illustration and are not intended to be limiting, with the true scope and spirit being indicated by the following claims.

What is claimed is:

1. A transdermal dispensing apparatus for a delivery of a plurality of compounds to aid in weight management, the apparatus comprising:
   a processor configured to:
      receive information associated with a subject;
      determine a first dosage for delivery of the plurality of compounds based on the received information; and
      determine a first timing for the delivery of the plurality of compounds based on the received information;
      receive input from the subject;
      determine a second dosage based on the received input; and
      determine a second timing based on the received input; and
   a dispensing unit communicatively coupled to the processor, the dispensing unit configured to:
      deliver the plurality of compounds transdermally to the subject based on the determined first and second dosages and the determined first and second timings.

2. The apparatus of claim 1, wherein the plurality of compounds includes one or more of:
   an appetite suppressant, wherein the appetite suppressant includes one or more of: diethylpropion, oxymetazoline, phentermine, rimonabant, sibutramine, bitter orange, chromium, forskolin, hydroxycitric acid, glucomannan, guar gum, or hoodia;
   a metabolic stimulator, wherein the metabolic stimulator includes one or more of: caffeine, bitter orange, calcium, chromium, conjugated linoleic acid, fucoxanthin, green coffee bean extract, pyruvate, raspberry ketone, white kidney bean, yohimbe, L-Tyrosine, L-Carnitine, green tea, resveratrol, nootkatone, or capsaicin; and/or
   a satiating compound, wherein the satiating compound includes one or more of: cholecystokinin, glucagon-like peptide 1, peptide YY, oxyntomodulin, apolipoprotein A-IV, enterostatin, bombesin-family peptides such as gastrin-releasing peptide and neuromedin B, amylin, leptin, glucomannan, guar gum, or chitosan.

3. The apparatus of claim 1, wherein the compound is an appetite suppressant, and wherein the processor and the dispensing unit are configured to deliver the appetite suppressant between mealtimes.

4. The apparatus of claim 1, wherein the processor is further configured to:
   receive one or more of: the first and second dosages or the first and second timings from a computing device communicatively coupled to the apparatus.

5. The apparatus of claim 1, further comprising a storage unit for the plurality of compounds.

6. The apparatus of claim 5, wherein the storage unit comprises one or more cartridges for each of the plurality of compounds, and wherein the one or more cartridges include one or more of: a refillable cartridge, a replaceable cartridge, a nonrefillable cartridge, or a nonreplaceable cartridge.

7. The apparatus of claim 6, wherein the dispensing unit comprises one or more dispensers coupled to corresponding one or more cartridges.

8. The apparatus of claim 6, wherein the dispensing unit comprises a single dispenser coupled to the one or more cartridges.

9. The apparatus of claim 1, wherein the dispensing unit comprises one or more of: an array of dispensers, a piezoelectric dispenser, or a Joule heating dispenser.

10. The apparatus of claim 1, further comprising a power source, wherein the power source corresponds to one or more of: a single use battery, a rechargeable battery, a replaceable battery, a kinetic energy harvesting device, a body heat conversion device, or a solar power device.

11. The apparatus of claim 1, further comprising a display device, wherein the display device is configured to display data associated with the delivery of the plurality of compounds, wherein data associated with the delivery of the plurality of compounds includes one or more of: the first and second dosages for the delivery of the plurality of compounds, the first and second timings for the delivery of the plurality of compounds, a current time, a fill-status of a storage unit, or a charge of a power source.

12. The apparatus of claim 1, further comprising one or more sensors, wherein the one or more sensors includes at least one of an accelerometer, a heart rate sensor, a thermometer, or a blood pressure sensor.

13. A system for a delivery of a plurality of compounds to aid in weight management, the system comprising:

a controller configured to:
  analyze information associated with a subject;
  determine a first dosage for delivery of the plurality of compounds based on the analysis; and
  determine a first timing for the delivery of the plurality of compounds based on the analysis;
  receive input from the subject;
  determine a second dosage based on the received input; and
  determine a second timing based on the received input; and
a delivery apparatus comprising:
  a storage unit;
  a processor configured to receive the determined first and second dosages and the determined first and second timings from the controller; and
  a dispensing unit configured to deliver the plurality of compounds transdermally to the subject based on the determined first and second dosages and the determined first and second timings.

14. The system of claim 13, wherein the plurality of compounds includes one or more of:
  an appetite suppressant, wherein the appetite suppressant includes one or more of: diethylpropion, oxymetazoline, phentermine, rimonabant, sibutramine, bitter orange, chromium, forskolin, hydroxycitric acid, glucomannan, guar gum, or hoodia;
  a metabolic stimulator, wherein the metabolic stimulator includes one or more of: caffeine, bitter orange, calcium, chromium, conjugated linoleic acid, fucoxanthin, green coffee bean extract, pyruvate, raspberry ketone, white kidney bean, yohimbe, L-Tyrosine, L-Carnitine, green tea, resveratrol, nootkatone, or capsaicin; and/or
  a satiating compound, wherein the satiating compound includes one or more of: cholecystokinin, glucagon-like peptide 1, peptide YY, oxyntomodulin, apolipoprotein A-IV, enterostatin, bombesin-family peptides such as gastrin-releasing peptide and neuromedin B, amylin, leptin, glucomannan, guar gum, or chitosan.

15. The system of claim 13, wherein the compound is an appetite suppressant, and wherein the controller and the delivery apparatus are configured to deliver the appetite suppressant between mealtimes.

16. The system of claim 13, wherein the compound is a metabolic stimulator, and wherein the controller and the delivery apparatus are configured to deliver the metabolic stimulator based on a comparison of a daily calorie intake and a recommended daily calorie intake.

17. The system of claim 13 further comprising one or more sensors, wherein the controller is further configured to:
  receive an input from the one or more sensors;
  update the information associated with the subject based on the input from the one or more sensors;
  analyze the updated information associated with the subject; and
  determine an updated first dosage and an updated first timing for individual delivery of the plurality of compounds based on the analysis.

18. The system of claim 17, wherein the one or more sensors are one of: an accelerometer, a heart rate sensor, a thermometer, or a blood pressure sensor.

19. The system of claim 13, wherein the storage unit comprises one or more cartridges for each of the plurality of compounds, and wherein the one or more cartridges include a refillable cartridge, a replaceable cartridge, a nonrefillable cartridge, or a nonreplaceable cartridge.

20. The system of claim 19, wherein the dispensing unit comprises a single dispenser coupled to the one or more cartridges.

21. The system of claim 19, wherein the dispensing unit comprises one or more dispensers coupled to corresponding one or more cartridges.

22. The system of claim 13, wherein the dispensing unit comprises one or more of: an array of dispensers, a piezoelectric dispenser, or a Joule heating dispenser.

23. The system of claim 13, further comprising a display device, wherein the display device is configured to display data associated with the delivery of the plurality of compounds, and wherein data associated with the delivery of the plurality of compounds includes one or more of: the first and second dosages for the delivery of the plurality of compounds, the first and second timings for the delivery of the plurality of compounds, a current time, a fill-status of a storage unit, or a charge of a power source.

24. A method for a delivery of a plurality of compounds to aid in weight management, the method comprising:
  receiving the plurality of compounds comprising an appetite suppressant, a metabolic stimulator, and a satiating compound;
  receiving information associated with a subject;
  determining a first dosage for delivery of the plurality of compounds based on the received information;
  determining a first timing for the delivery of the plurality of compounds based on the received information;
  receiving input from the subject;
  determining a second dosage based on the received input;
  determining a second timing based on the received input; and
  delivering the plurality of compounds transdermally based on the determined first and second dosages and the determined first and second timings.

25. The method of claim 24, wherein receiving the information associated with the subject comprises:
  receiving one or more of: a current weight, a goal weight, one or more average mealtimes, a sleep schedule, an actual calorie intake, a recommended calorie intake, and/or calories burned.

26. The method of claim 24, further comprising:
  receiving one or more pre-determined dosages and one or more pre-determined timings; and
  determining the first dosage and the first timing based on the pre-determined dosages and pre-determined timings.

27. The method of claim 24, wherein receiving the plurality of compounds comprises:
  storing the plurality of compounds in one or more cartridges.

* * * * *